(12) United States Patent
Stahmann

(10) Patent No.: US 7,955,269 B2
(45) Date of Patent: Jun. 7, 2011

(54) METHOD AND APPARATUS FOR PULMONARY ARTERY PRESSURE SIGNAL ISOLATION

(75) Inventor: Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 12/489,233

(22) Filed: Jun. 22, 2009

(65) Prior Publication Data

US 2009/0254138 A1  Oct. 8, 2009

Related U.S. Application Data

(62) Division of application No. 11/249,624, filed on Oct. 13, 2005, now Pat. No. 7,566,308.

(51) Int. Cl.
A61B 5/02 (2006.01)
(52) U.S. Cl. ........................................ 600/486; 600/485
(58) Field of Classification Search .................. 600/485, 600/486
See application file for complete search history.

(56) References Cited

U.S. PATENT DOCUMENTS

| | | | |
|---|---|---|---|
| 4,588,404 A | 5/1986 | Lapeyre | |
| 5,003,976 A | 4/1991 | Alt | |
| 5,485,827 A | 1/1996 | Zapol et al. | |
| 5,697,375 A | 12/1997 | Hickey | |
| 5,704,891 A | 1/1998 | Mussivand | |
| 5,758,652 A | 6/1998 | Nikolic | |
| 5,913,826 A | 6/1999 | Blank | |
| 6,159,156 A * | 12/2000 | Van Bockel | 600/485 |
| 6,251,062 B1 | 6/2001 | Leysieffer | |
| 6,456,256 B1 | 9/2002 | Amundson et al. | |
| 6,656,966 B2 | 12/2003 | Garvey et al. | |
| 6,804,656 B1 | 10/2004 | Rosenfeld et al. | |
| 6,832,113 B2 | 12/2004 | Belalcazar | |
| 6,865,419 B2 | 3/2005 | Mulligan et al. | |
| 7,001,337 B2 | 2/2006 | Dekker | |
| 7,335,161 B2 | 2/2008 | Von Arx et al. | |
| 7,566,308 B2 | 7/2009 | Stahmann | |
| 2004/0147969 A1 | 7/2004 | Mann et al. | |
| 2005/0038332 A1* | 2/2005 | Saidara et al. | 600/347 |
| 2005/0159789 A1 | 7/2005 | Brockway et al. | |
| 2005/0283208 A1 | 12/2005 | Von Arx et al. | |
| 2006/0009818 A1 | 1/2006 | Von Arx et al. | |

(Continued)

FOREIGN PATENT DOCUMENTS

WO    WO-97/11637 A1    4/1997

(Continued)

OTHER PUBLICATIONS

"U.S. Appl. No. 11/249,624, Final Office Action mailed Dec. 29, 2008", 12 pgs.

(Continued)

*Primary Examiner* — Charles A Marmor, II
*Assistant Examiner* — Christian Jang
(74) *Attorney, Agent, or Firm* — Schwegman, Lundberg & Woessner, P.A.

(57) ABSTRACT

An implantable system senses a pulmonary artery pressure (PAP) signal using an implantable sensor placed in the pulmonary artery and isolates a plurality of signals from the PAP signal for diagnostic and/or therapeutic use. Each signal is extracted from the PAP signal using its known frequency characteristics and/or timing relationship with one or more detectable events.

19 Claims, 19 Drawing Sheets

U.S. PATENT DOCUMENTS

| | | |
|---|---|---|
| 2006/0041281 A1 | 2/2006 | Von Arx et al. |
| 2006/0064133 A1 | 3/2006 | Von Arx et al. |
| 2006/0064134 A1 | 3/2006 | Mazar et al. |
| 2006/0064142 A1 | 3/2006 | Chavan et al. |
| 2006/0064143 A1 | 3/2006 | Von Arx et al. |
| 2006/0122522 A1 | 6/2006 | Chavan et al. |
| 2007/0088221 A1 | 4/2007 | Stahmann |

FOREIGN PATENT DOCUMENTS

| | | |
|---|---|---|
| WO | WO-2007/047287 A2 | 4/2007 |

OTHER PUBLICATIONS

"U.S. Appl. No. 11/249,624, Non-Final Office Action mailed Jun. 25, 2008", 9 pgs.

"U.S. Appl. No. 11/249,624, Notice of Allowance mailed Mar. 23, 2009", 6 pgs.

"U.S. Appl. No. 11/249,624, Response filed Feb. 23, 2009 to Final Office Action mailed Dec. 29, 2008", 8 pgs.

"U.S. Appl. No. 11/249,624, Response filed Apr. 30, 2008 to Restriction Requirement Mar. 31, 2008", 28 pgs.

"U.S. Appl. No. 11/249,624, Response filed Sep. 22, 2008 to Non-Final Office Action mailed Jun. 25, 2008", 9 pgs.

"U.S. Appl. No. 11/249,624, Restriction Requirement Mar. 31, 2008", 7 pgs.

"European Application Serial No. 06816694.1, Communication mailed Aug. 26, 2008", 2 pgs.

"European Application Serial No. 06816694.1, Response filed Mar. 3, 2009 to Communication mailed Aug. 26, 2008", 18 pgs.

"International Application No. PCT/US2006/039663, International Search Report mailed Oct. 4, 2007", 5 pgs.

"PCT Application No. PCT/US2006/039663, Written Opinion mailed Oct. 4, 2007", 10 pgs.

Adamson, P. B, et al., "Ongoing Right Venticular Hemodynamics in Heart Failure: Clinical Value of Measurements Derived From an Implantable Monitoring System.", *Journal of the american college of cardiology*, vol. 41 (4), (Feb. 19, 2003), 565-571.

Dulak, S B, "PA catheters. What the waveforms reveal", *RN*, 66(9), (Sep. 2003), 56-63; quiz 64.

Gibbs, J S, "Diurnal variation of pulmonary artery pressure in chronic heart failure", *British Heart Journal*, 62(1), (Jul. 1989), 30-35.

Libbus, Imad, "Expandable Stimulation Electrode with Integrated Pressure Sensor and Methods Related Thereto", U.S. Appl. No. 10/746,846, filed Feb. 14, 2006, 43 pgs.

Lin, K.-P., et al., "Adaptive Noise Reduction for Pulmonary Blood Pressure", *Proceedings of the Annual International Conference of the IEEE Engineering in Medicine and Biology Society*, (Nov. 4, 1988), 82-83.

Pott, F, "Middle cerebral artery blood velocity during a valsalva maneuver in the standing position", *J Appl Physiol.*, 88(5), (May 2000), 1545-1550.

Stahmann, Jeffrey E, "Detection of Hypovolemia Using Implantable Medical Device", U.S. Appl. No. 11/249,611, filed Oct. 13, 2005, 58 pgs.

Steinhaus, D. M, et al., "Initial Experience With an Implantable Hemodynamic Monitor", *Circulation*, 93(4), (Feb. 15, 1996), 745-752.

"European Application No. 06816694.1, Office Action mailed on Mar. 12, 2010", 4 pages.

\* cited by examiner

METHOD AND APPARATUS FOR PULMONARY ARTERY PRESSURE SIGNAL ISOLATION

CROSS REFERENCE TO RELATED APPLICATION

This application is a divisional of U.S. application Ser. No. 11/249,624, filed Oct. 13, 2005, now issued as U.S. Pat. No. 7,566,308, which is hereby incorporated by reference in its entirety.

TECHNICAL FIELD

This document relates generally to medical systems and particularly, but not by way of limitation, to such a system sensing a pulmonary artery pressure (PAP) signal and isolating multiple signals for diagnostic and/or therapeutic uses from the sensed PAP signal.

BACKGROUND

Blood pressure indicates a person's cardiovascular conditions and hemodynamic performance and is sensed for various diagnostic, monitoring, and therapy-control purposes. A blood pressure signal sensed from a person includes signal components originated from various physiological and environmental sources. For example, an intravascular pressure sensor may sense a pressure signal including components of various origins including, but not limited to, cardiac activities, pulmonary activities, posture, exercise, weather, altitude, atmospheric pressure, operation of a respirator, Valsalva and Mueller maneuvers, cardiopulmonary resuscitation (CPR), and various cardiovascular and other physiological conditions. Most of such components of the pressure signal each have diagnostic and/or therapeutic value. However, each component of the pressure signal may be a signal for one diagnostic, monitoring, or therapy-control purpose but must be excluded for another diagnostic, monitoring, or therapy-control purpose. In other words, each component of the pressure signal may be a signal for one purpose but a noise for another purpose.

Different components of a sensed blood pressure signal may provide information needed for substantially different purposes in the same medical system performing various diagnostic, monitoring, and/or therapy-control purposes. Therefore, there is a need for a system that provides for efficient processing of the sensed blood pressure signal for each purpose.

SUMMARY

An implantable medical device processes a sensed pulmonary artery pressure (PAP) signal to isolate a plurality of signals from the PAP signal for diagnostic, monitoring, and/or therapeutic uses. Each signal is a component of the PAP signal having one or more characteristics allowing for its separation from other components of the PAP signal. In one embodiment, an implantable pressure sensor is placed in the pulmonary artery to sense the PAP signal.

In one embodiment, a system for processing signals sensed by an implantable PAP sensor includes a wireless communication circuit and a PAP signal processor. The wireless communication circuit receives a PAP signal from the implantable PAP sensor. The PAP signal processor includes a signal isolation module that isolates a plurality of signals from the PAP signal.

In one embodiment, an implantable system includes an implantable PAP sensor and an implantable medical device. The implantable sensor is configured for placement in the pulmonary artery to sense a PAP signal. The implantable medical device includes a PAP signal processor. The PAP signal processor includes a signal isolation module that isolates a plurality of signals from the PAP signal.

In one embodiment, a method for processing a PAP signal is provided. A PAP signal is received from an implantable PAP sensor through a wireless communication link. Multiple signals are isolated from the PAP signal for diagnostic, monitoring, and/or therapeutic uses.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION

Figure 1:
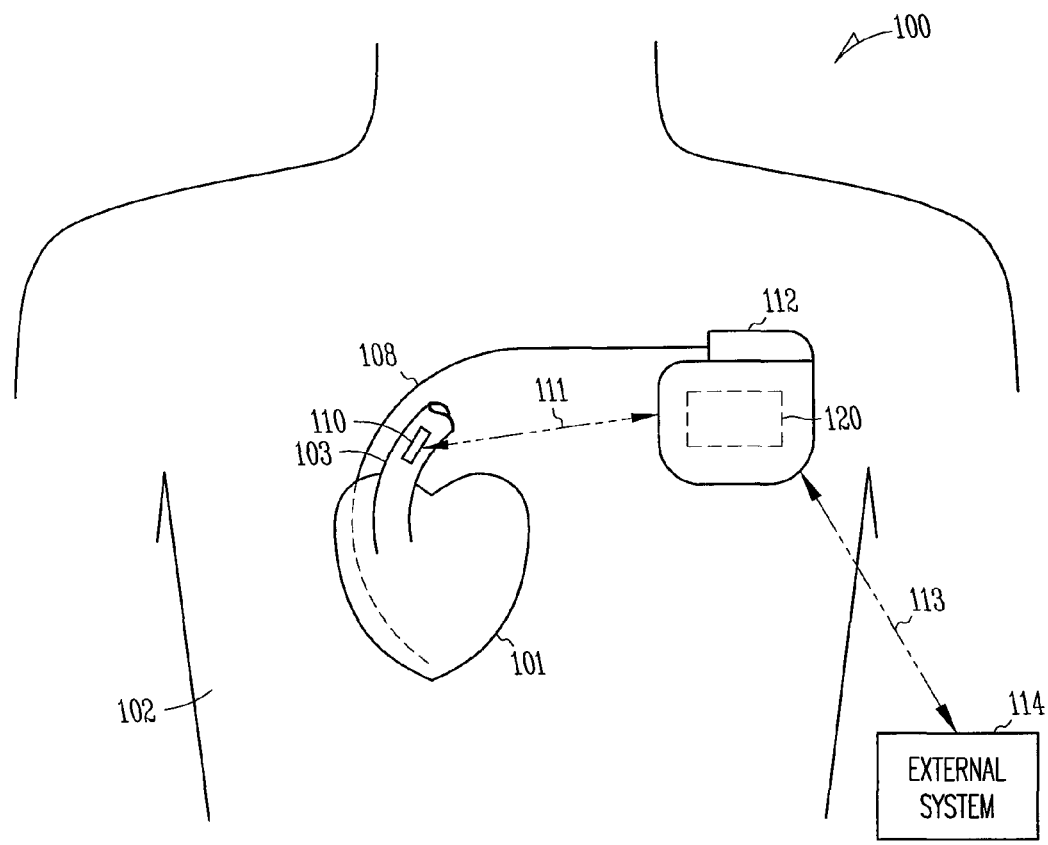
FIG. 1 is an illustration of an embodiment of a medical system that senses a PAP signal using an implantable sensor and portions of an environment in which the medical system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their legal equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

This document discusses a sensor signal processing system that isolates various signals from a PAP signal. A physiological sensor senses the PAP signal as a physiological signal indicative of PAP. The PAP signal includes signal components having various signal and noise sources that are physiological and environmental in nature. Such signal components are related to, for example, cardiac activities, respiratory activities, atmospheric pressure, weather, altitude, posture, Valsalva and Mueller maneuvers, exercise, CPR, external respiratory therapy, coughs, and sneezes. Isolation of some of these signal components from the PAP signal allows for their therapeutic or diagnostic use. For example, a respiratory signal including isolated respiratory components of the PAP signal provides an accurate measure of the patient's respiratory rate and respiratory cycle phase. This respiratory signal may also provide for estimation of tidal volume, minute ventilation, and other respiratory parameters. Additionally, the isolated respiratory component allows proper interpretation of the PAP signal and other signals isolated from the PAP signal. For example, to avoid the effect of respiration, PAP readings are taken at the end of the expiratory phase of a respiratory cycle. A signal indicative of the expiratory phase provides a timing trigger for proper sampling of the PAP signal. Isolation of a low-frequency (near DC) component of the PAP signal provides a measure of the mean PAP and relatively slow moving signals such as atmospheric pressure. Isolation of the cardiac component from the PAP signal provides greater dynamic range of the PAP signal because the DC offset and the respiratory component is eliminated. A cardiac signal including isolated cardiac components of the PAP signal also provides for calculation of mechanical and electro-mechanical cardiac timing intervals. Isolated signals indicative of changes in PAP immediately before, during, and immediately after the performance of intrathoracic pressure maneuvers such as Valsalva and Mueller maneuvers provide for assessment of cardiac performance, including detection of potential heart failure.

The sensor signal processing system isolates desired signals from the PAP signal by using distinctive characteristics of each signal to be isolated. The isolated signals serve multiple diagnostic, monitoring, and/or therapy-control purposes. In one embodiment, the physiological sensor that senses the PAP signal is an implantable PAP sensor that senses the PAP. In other embodiments, the physiological sensor that senses the PAP signal is an implantable or external sensor that senses the PAP or a signal representative of the PAP. In one embodiment, an implantable medical device receives the PAP signal from the physiological sensor and includes the sensor signal processing system to isolate a plurality of signals from the PAP signal. In another embodiment, an external device receives the PAP signal from the physiological sensor and includes the sensor signal processing system to isolate a plurality of signals from the PAP signal.

FIG. 1 is an illustration of one embodiment of a medical system 100 and portions of an environment in which system 100 operates. System 100 includes an implantable PAP sensor 110, an implantable medical device 112, an external system 114, a communication link 111 between PAP sensor 110 and implantable medical device 112, and a communication link 113 between implantable medical device 112 and external system 114.

As illustrated in FIG. 1, implantable PAP sensor 110 and implantable medical device 112 are implanted in a body 102 that has a pulmonary artery 103 connected to a heart 101. The right ventricle of heart 101 pumps blood through pulmonary artery 103 to the lungs of body 102 to get oxygenated. Implantable PAP sensor 110 is a pressure sensor configured for being mounted on a portion of the interior wall of pulmonary artery 103 to sense a PAP signal. The sensed PAP signal is transmitted to implantable medical device 112 through communication link 111. In one embodiment, communication link 111 includes a wired communication link formed by a lead connected between implantable PAP sensor 110 and implantable medical device 112. In another embodiment, communication link 111 includes an intra-body wireless telemetry link. Implantable medical device 112 includes a sensor signal processing system that receives and processes the PAP signal sensed by implantable PAP sensor 110. The sensor signal processing system includes a PAP signal processor 120 that isolates a plurality of signals of substantially different types from the PAP signal for diagnostic, monitoring, and/or therapy-control uses. In various embodiments, implantable medical device 112 is an implantable CRM device including one or more of a physiological monitor, a pacemaker, a cardioverter/defibrillator, a cardiac resynchronization therapy (CRT) device, a cardiac remodeling control therapy (RCT) device, a neural stimulator, a drug delivery device or a drug delivery controller, and a biological therapy device. In various embodiments in which one or more signals in addition to the PAP signal are sensed, and/or one or more therapies are delivered, a lead system 108 provides for electrical and/or other connections between body 102 and implantable medical device 112. In various embodiments, lead system 108 includes leads for sensing physiological signals and delivering pacing pulses, cardioversion/defibrillation shocks, neural stimulation pulses, pharmaceutical agents, biological agents, and/or other types of energy or substance for treating cardiac disorders. In one embodiment, as illustrated in FIG. 1, lead system 108 provides for such electrical and/or other connections between heart 101 and implantable medical device 112.

External system 114 allows a user such as a physician or other caregiver to control the operation of implantable medical device 112 and obtain information acquired by implantable medical device 112. In one embodiment, external system 114 includes a programmer communicating with implantable medical device 112 bi-directionally via communication link 113, which is a telemetry link. In another embodiment, external system 114 is a patient management system including an external device communicating with a remote device through a telecommunication network. The external device is within the vicinity of implantable medical device 112 and communicates with implantable medical device 112 bi-directionally via communication link 113. The remote device allows the user to monitor and treat a patient from a distant location. The patient monitoring system is further discussed below, with reference to FIG. 12.

Communication link 113 provides for data transmission from implantable medical device 112 to external system 114. This includes, for example, transmitting real-time physiological data acquired by implantable medical device 112, extracting physiological data acquired by and stored in implantable medical device 112, extracting therapy history data stored in implantable medical device 112, and extracting data indicating an operational status of implantable medical device 112 (e.g., battery status and lead impedance). The real-time and stored physiological data acquired by implantable medical device 112 include data representative of the PAP signal sensed by implantable PAP sensor 110. Telemetry link 113 also provides for data transmission from external system 114 to implantable medical device 112. This includes, for example, programming implantable medical device 112 to acquire physiological data, programming implantable medical device 112 to perform at least one self-diagnostic test (such as for a device operational status), and programming implantable medical device 112 to deliver at least one therapy.

In various embodiments, PAP signal processor 120, including its specific embodiments as discussed below, is implemented by hardware, software, or a combination of hardware and software. In various embodiments, PAP signal processor 120 includes elements such as those referred to as modules below that are each an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

It is to be understood that while system 100 is specifically discussed in this document as an illustrative example, the present subject matter is not limited to embodiments using an implantable PAP sensor and/or an implantable medical device that includes the sensor signal processing system. For example, the PAP signal can be sensed by a non-implantable sensor, and the sensor signal processing system can be implemented in a non-implantable device.

Figure 2:
FIG. 2 is a graph illustrating an exemplary PAP signal.

FIG. 2 is a graph illustrating an exemplary PAP signal 204. PAP signal 204 is primarily a cardiac signal including a respiratory signal component 205. PAP signal 204 represents the PAP, which changes with cardiac cycles. Respiratory signal component 205 indicates respiratory cycles. PAP signal 204 also includes signal components from various other sources such as atmospheric pressure, posture, weather, altitude, Valsalva maneuvers, and Mueller maneuvers.

Figure 3:
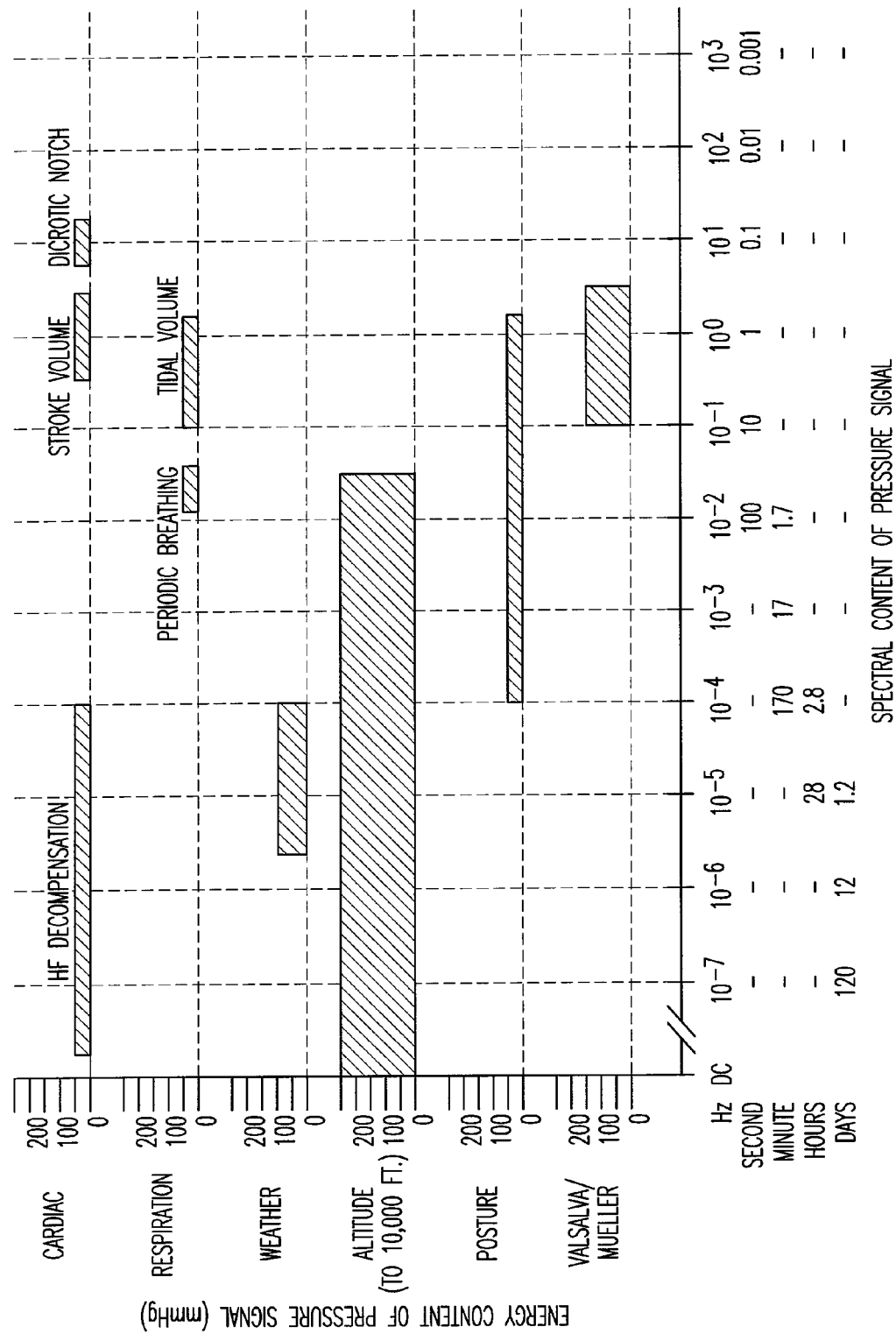
FIG. 3 is a graph illustrating amplitude and frequency characteristics of various components of a PAP signal.

FIG. 3 is a graph illustrating amplitude and frequency characteristics of various components of a PAP signal. Such characteristics provide for bases upon which various signals can be isolated from the PAP signal for diagnostic, monitoring, and/or therapy-control uses.

Figure 4:
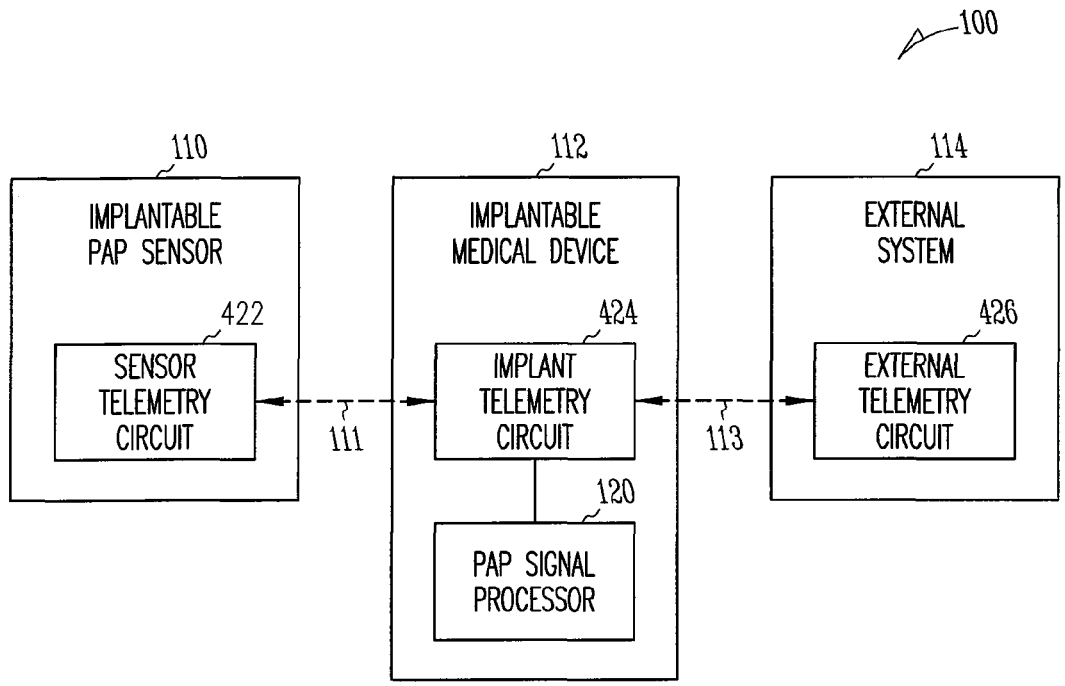
FIG. 4 is a block diagram illustrating an embodiment of portions of a circuit of the medical system of FIG. 1.

FIG. 4 is a block diagram illustrating an embodiment of portions of a circuit of system 100. Implantable PAP sensor 110 is an integrated circuit sensor that includes a sensor telemetry circuit 422, which is a wireless communication circuit, in addition to its pressure-sensing element. Implantable medical device 112 includes an implant telemetry circuit 424, in addition to PAP signal processor 120 and, if applicable, other sensing and/or therapeutic elements. In one embodiment, implant telemetry circuit 424 includes a sub-circuit supporting communication link 111 and another sub-circuit supporting communication link 113. External system 114 includes an external telemetry circuit 426, in addition to programming and other patient management elements.

In one embodiment, communication link 111 is an ultrasonic telemetry link. Sensor telemetry circuit 422 includes an ultrasonic telemetry transmitter that transmits the PAP signal by modulating an ultrasonic signal using the PAP signal and transmitting the modulated ultrasonic signal. Implant telemetry circuit 424 includes an ultrasonic telemetry receiver that receives the PAP signal by demodulating the modulated ultrasonic carrier signal. An example of an intra-body ultrasonic telemetry system is discussed in U.S. patent application Ser. No. 10/888,956, entitled "METHOD AND APPARATUS OF ACOUSTIC COMMUNICATION FOR IMPLANTABLE MEDICAL DEVICE," filed on Jul. 9, 2004, assigned to Cardiac Pacemakers, Inc., which is incorporated herein by reference in its entirety. In another embodiment, communication link 111 is a far-field radio-frequency (RF) telemetry link. Sensor telemetry circuit 422 includes a far-field RF telemetry transmitter that transmits the PAP signal by modulating an electromagnetic signal using the PAP signal and transmitting the modulated electromagnetic signal. Implant telemetry circuit 424 includes a far-field RF telemetry receiver that receives the PAP signal by demodulating the modulated electromagnetic carrier signal. In another embodiment, communication link 111 is an inductive telemetry link. Sensor telemetry circuit 422 includes an inductive telemetry transmitter that transmits the PAP signal by modulating a magnetic field using the PAP signal. Implant telemetry circuit 424 includes an inductive telemetry receiver that receives the PAP signal by demodulating the modulated magnetic field. In one embodiment, communication link 111 is a bidirectional telemetry link that allows for transmission of the PAP signal from implantable PAP sensor 110 to implantable medical device 112 as well as transmission of signals such as command signals from implantable medical device 112 to implantable PAP sensor 110 for controlling the operation of implantable PAP sensor 110. Sensor telemetry circuit 422 and implant telemetry circuit 424 each include an ultrasonic, far-field RF, or inductive telemetry transceiver to support communication link 111.

In various embodiments, communication link 113 is a bidirectional ultrasonic, far-field RF, or inductive telemetry link. Implant telemetry circuit 424 and external telemetry circuit 426 each include an ultrasonic, far-field RF, or inductive telemetry transceiver to support communication link 113.

Communication links 111 and 113 are illustrated in FIG. 3 and discussed above for illustrative but not restrictive purposes. Other communicating schemes are useable to transmit the sense PAP signal from implantable PAP sensor 110 to implantable medical device 112, from implantable medical device 112 to external system 114, or from implantable PAP sensor 110 to external system 114. In one embodiment, an insulated wire can provide an electrical connection between implantable PAP sensor 110 and implantable medical device 112 for transmitting the PAP signal. In another embodiment, implantable PAP sensor 110 communicates directly with external system 114 using an ultrasonic, far-field RF, or inductive telemetry link through which the PAP signal is transmitted.

Figure 5:
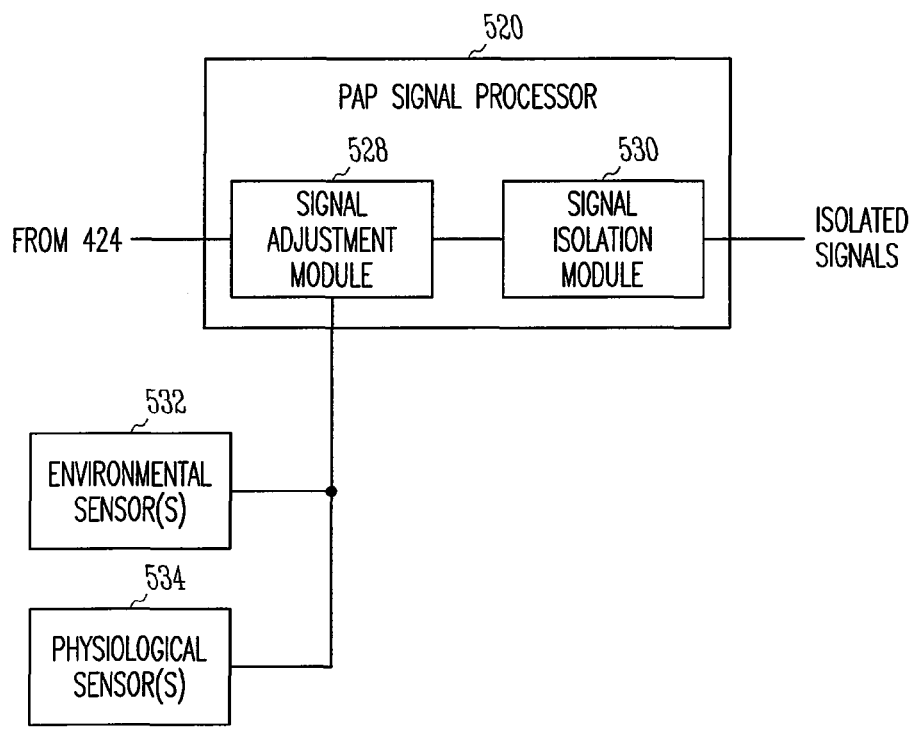
FIG. 5 is a block diagram illustrating an embodiment of a system for processing the PAP signal.

FIG. 5 is a block diagram illustrating an embodiment of a system for processing the PAP signal including a PAP signal processor 520, one or more environmental sensors 532, and one or more physiological sensors 534. PAP signal processor 520 is a specific embodiment of PAP signal processor 120. Environmental sensor(s) 532 and physiological sensor(s) 534 are each a sensor contained within implantable medical device 112 or coupled to implantable medical device 112 via an electrical or telemetry connection.

PAP signal processor 520 includes a signal adjustment module 528 and a signal isolation module 530. Signal adjustment module 528 adjusts the PAP signal by removing one or more unwanted signal components in preparation for isolation of a plurality of wanted signal components by signal isolation module 530. Environmental sensor(s) 532 sense one or more environmental signals related to the one or more unwanted signal components that have one or more environmental origins. Physiological sensor(s) 534 sense one or more physiological signals related to the one or more unwanted signal components that have one or more physiological origins.

In one embodiment, PAP signal processor 520 digitizes the PAP signal received from implant telemetry circuit 424 before further processing. A preamplifier and filter circuit receives the PAP signal and amplifies and filters the PAP signal. In various embodiments, the preamplifier and filter circuit is part of PAP signal processor 520, part of implant telemetry circuit 424, or distributed in both PAP signal processor 520 and implant telemetry circuit 424. The amplified and filtered PAP signal is then digitized using an analog-to-digital converter (ADC) before being adjusted by signal adjustment module 528. In one embodiment, the preamplifier and filter circuit has a gain in a range of approximately 1 to 10 and a pass-band with a low cutoff frequency in a range of approximately 0.000001 Hz to 0.1 Hz and a high cutoff frequency in a range of approximately 3 Hz to 30 Hz. The ADC has a sample rate in a range of approximately 5 Hz to 50 Hz. In a specific embodiment, the preamplifier and filter circuit has a gain of approximately 1 and a pass-band with a low cutoff frequency of approximately 0.01 Hz and a high cutoff frequency of approximately 5 Hz. The ADC has a sample rate of approximately 20 Hz.

Figure 6:
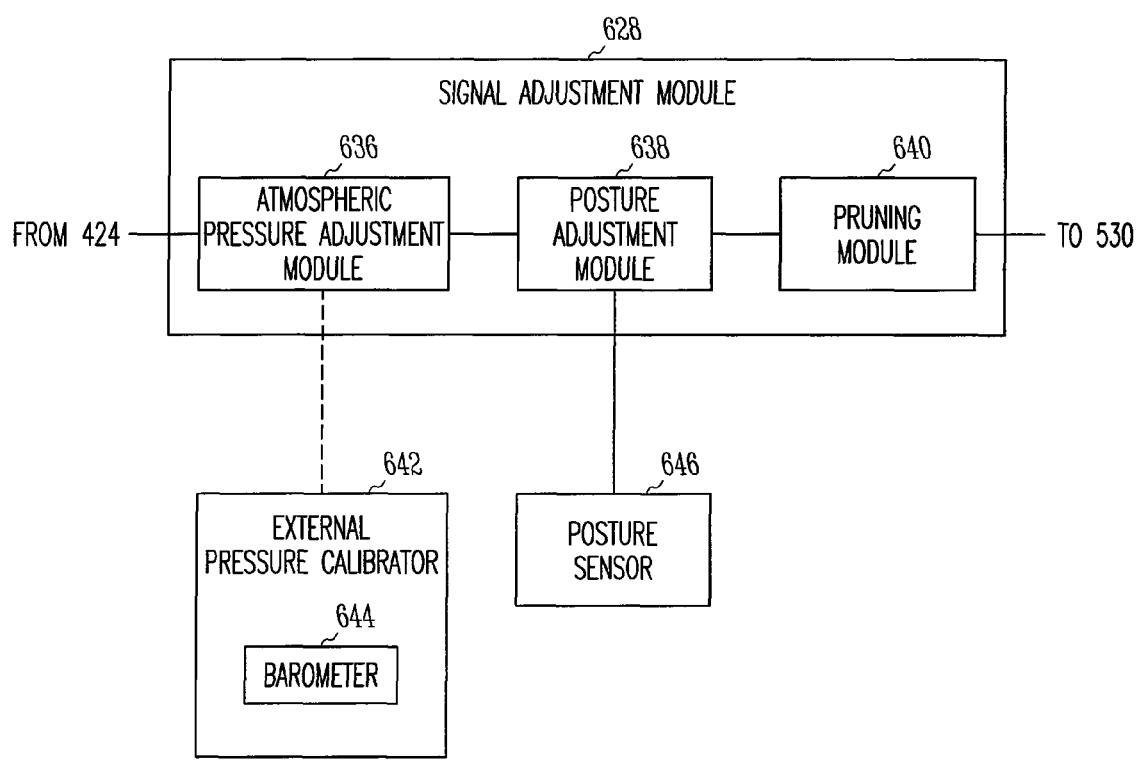
FIG. 6 is a block diagram illustrating an embodiment of portions of the system of FIG. 5 for adjusting the PAP signal.

FIG. 6 is a block diagram illustrating an embodiment of a system for adjusting the sensed PAP signal including a signal adjustment module 628, an external pressure calibrator 642, and a posture sensor 646. Signal adjustment module 628 is a specific embodiment of signal adjustment module 528. External pressure calibrator 642 is one of environmental sensor(s) 532. Posture sensor 646 is one of physiological sensor(s) 534.

Signal adjustment module 628 includes an atmospheric pressure adjustment module 636, a posture adjustment module 638, and a pruning module 640. Atmospheric pressure adjustment module 636 adjusts the PAP signal using an atmospheric pressure sensed by external pressure calibrator 642, which includes a barometer 644. In one embodiment, external pressure calibrator 642 is a portable device to be placed near implantable medical device 112 and communicates with atmospheric pressure adjustment module 636 via telemetry. Posture adjustment module 638 adjusts the PAP signal for effects related to posture as sensed by posture sensor 646. Pruning module 640 algorithmically prunes predetermined type outlier components from the sensed PAP signal.

In various embodiments, signal adjustment module 628 includes one or more of atmospheric pressure adjustment module 636, posture adjustment module 638, pruning module 640, and other adjustment modules for adjusting the PAP signal. In one embodiment, implantable medical device 112 includes a respiratory sensor such as an impedance sensor sensing an impedance signal indicative of respiratory cycles, and signal adjustment module 628 includes a respiratory adjustment module to remove the effect of respiration in the PAP signal.

Figure 7:
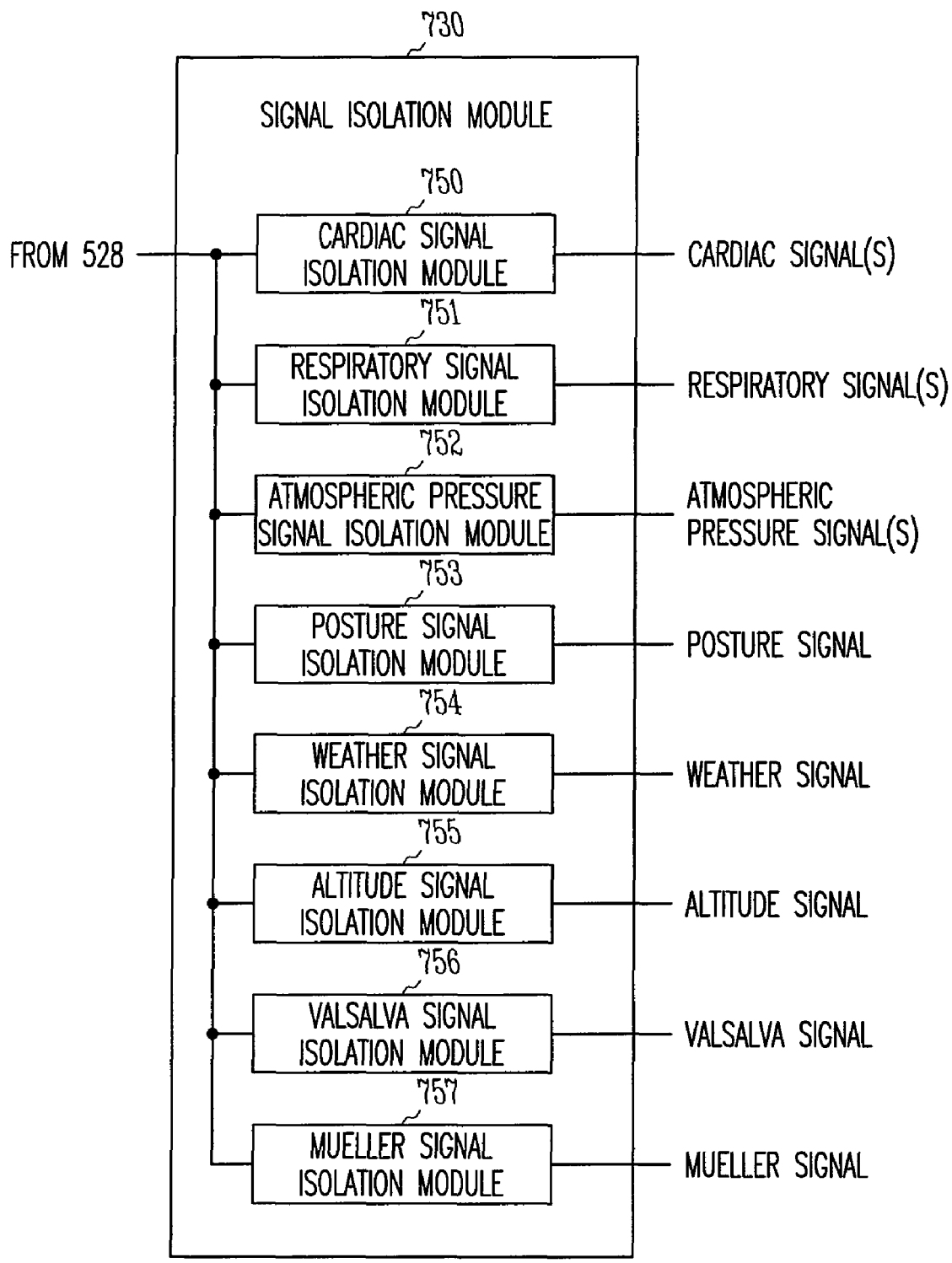
FIG. 7 is a block diagram illustrating an embodiment of portions of the system of FIG. 5 for isolating signals from the PAP signal.

FIG. 7 is a block diagram illustrating an embodiment of a signal isolation module 730, which is a specific embodiment of signal isolation module 530. As illustrated in FIG. 7, signal isolation module 730 includes a cardiac signal isolation module 750 that isolates one or more cardiac signals from the sensed PAP signal, a respiratory signal isolation module 751 that isolates one or more respiratory signals from the PAP signal, an atmospheric pressure signal isolation module 752 that isolates an atmospheric pressure signal from the PAP signal, a posture signal isolation module 753 that isolates a posture signal from the PAP signal, a weather signal isolation module 754 that isolates a weather signal from the PAP signal, an altitude signal isolation module 755 that isolates an altitude signal from the PAP signal, a Valsalva signal isolation module 756 that isolates a Valsalva signal from the PAP signal, and a Mueller signal isolation module 757 that isolates a Mueller signal from the PAP signal. In various other embodiments, signal isolation module 730 includes any one or more of cardiac signal isolation module 750, respiratory signal isolation module 751, atmospheric pressure signal isolation module 752, posture signal isolation module 753, weather signal isolation module 754, altitude signal isolation module 755, Valsalva signal isolation module 756, and Mueller signal isolation module 757.

The cardiac, respiratory, atmospheric pressure, posture, weather, altitude, Valsalva, and Mueller signals are each isolated for direct and/or indirect diagnostic monitoring, and/or therapy-control uses. For example, the one or more cardiac signals are indicative of cardiac performance parameters such as stroke volume as well as heart failure (HF) decompensation. The one or more respiratory signals are indicative of pulmonary performance parameters such as tidal volume as well as periodic breathing. Parameters derived from such cardiac and respiratory signals are useable for monitoring a patient's cardiopulmonary health, including state of HF, and/or for controlling one or more therapies for improving hemodynamic performances. The posture signal is used to indirectly detect posture changes or to remove effects of posture in sensed physiological signals such as various blood pressure signals. The atmospheric, weather, and altitude signals are used to indirectly detect atmospheric, weather, and altitude changes and to remove effects of environmental factors in sensed physiological signals such as various blood pressure signals. The Valsalva signal includes components of the PAP signal that indicates changes in PAP immediately before, during, and immediately after a Valsalva maneuver. The Mueller signal includes components of the PAP signal that indicates changes in PAP immediately before, during, and immediately after a Mueller maneuver. The Valsalva and Muller signals each provide for assessment of cardiac performance, including detection or prediction of HF. An example of assessing cardiac performance using Valsalva maneuver is discussed in U.S. patent application Ser. No. 10/782,642, entitled "SYSTEM AND METHOD FOR ASSESSING CARDIAC PERFORMANCE THROUGH TRANSCARDIAC IMPEDANCE MONITORING," filed on Feb. 19, 2004, assigned to Cardiac Pacemakers, Inc., which is incorporated by reference herein in its entirety. In various embodiments, the content and characteristics of the cardiac, respiratory, atmospheric pressure, posture, weather, altitude, Valsalva, and Mueller signals to be isolated from the PAP signal are each determined based on the intended use of that signal in diagnosis, monitoring, and/or therapy-control.

Signal isolation modules 750-757 each isolate one or more signals from the PAP signal by using amplitude and frequencies characteristics of the various components of the PAP signal, such as these illustrated in FIG. 3, as well as timing relationships between those one or more signals and other detectable signals or events. Isolation of several cardiac and respiratory signals is discussed with reference to FIGS. 8-10 as specific examples, but not limitations, to illustrate how signal isolation modules 750-757 isolate the one or more signals from the PAP signal. Upon reading and understanding this document, those skilled in the art will understand how to isolate signals such as cardiac, respiratory, atmospheric pressure, posture, weather, altitude, Valsalva, and Mueller signals, for specifically intended uses in diagnosis, monitoring, and/or therapy-control by using techniques and structural approaches identical or similar to those illustrated in FIGS. 8-10.

Figure 8:
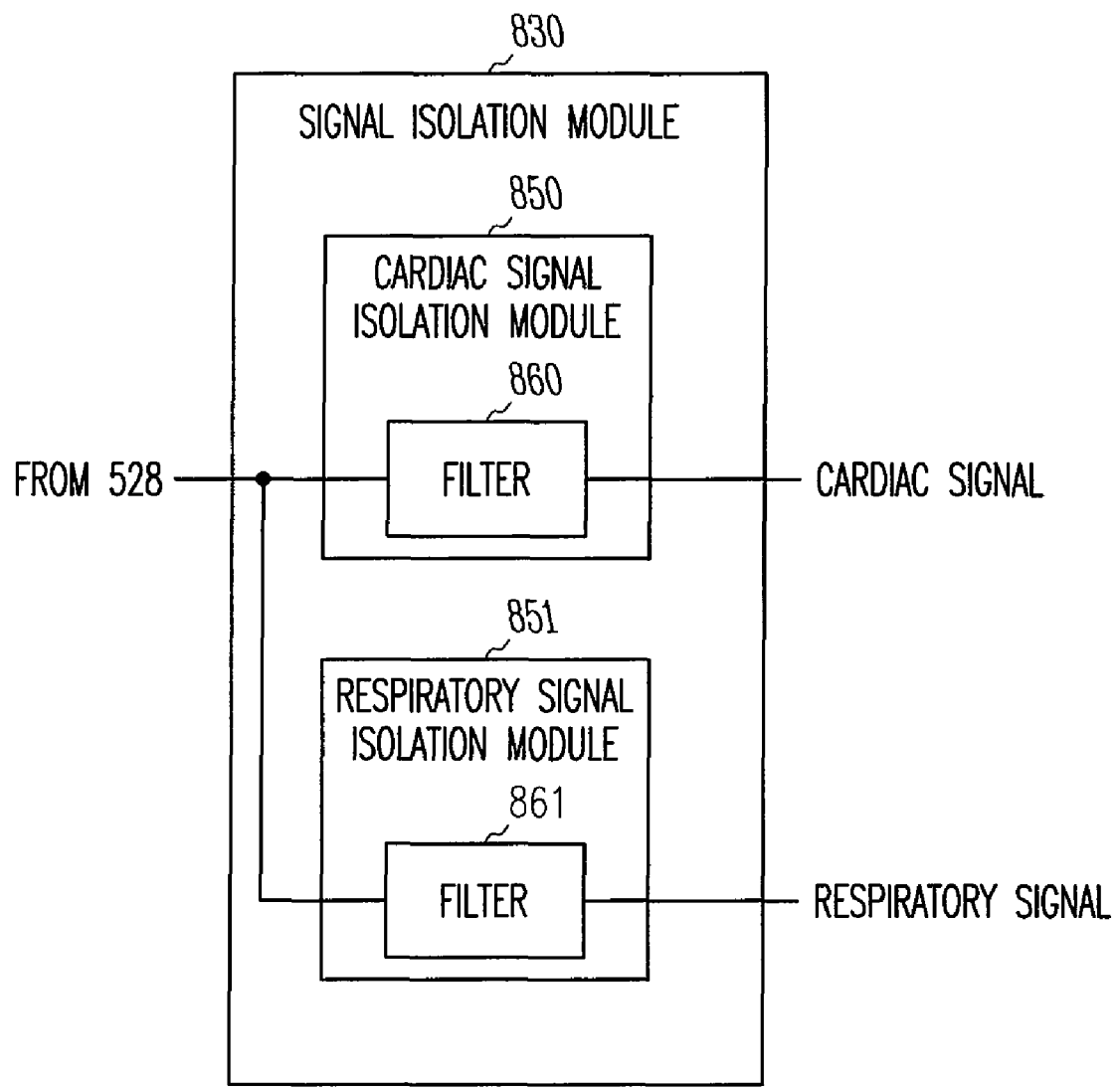
FIG. 8 is a block diagram illustrating a specific embodiment of portions of the system of FIG. 5 for isolating signals from the PAP signal.

FIG. 8 is a block diagram illustrating an embodiment of a signal isolation module 830, which is another specific embodiment of signal isolation module 530. Signal isolation module 830 includes a cardiac signal isolation module 850 and a respiratory signal isolation module 851.

Cardiac signal isolation module 850 includes a filter 860. In one embodiment, filter 860 includes a band-pass filter having a predetermined pass band. In a specific embodiment, the band-pass filter is used to isolate a cardiac signal including the dicrotic notch. The pass band has a low cutoff frequency of approximately 0.3 Hz and a high cutoff frequency of approximately 20 Hz. In another specific embodiment, the band-pass filter is used to isolate a cardiac signal including heart failure (HF) decompensation. The pass band has a low cutoff frequency of approximately 0.0000001 Hz and a high cutoff frequency of approximately 0.0001 Hz.

Respiratory signal isolation module 851 includes a filter 861. In one embodiment, filter 861 includes a band-pass filter having a predetermined pass band. In a specific embodiment, the band-pass filter is used to isolate a respiratory signal indicative of tidal volume by removing the weather and altitude components of the PAP signal. The pass band has a low cutoff frequency of approximately 0.08 Hz and a high cutoff frequency of approximately 5 Hz. In another specific embodiment, the band-pass filter is used to isolate a respiratory signal indicative of periodic breathing. The pass band has a low cutoff frequency of approximately 0.01 Hz and a high cutoff frequency of approximately 0.05 Hz.

Figure 9:
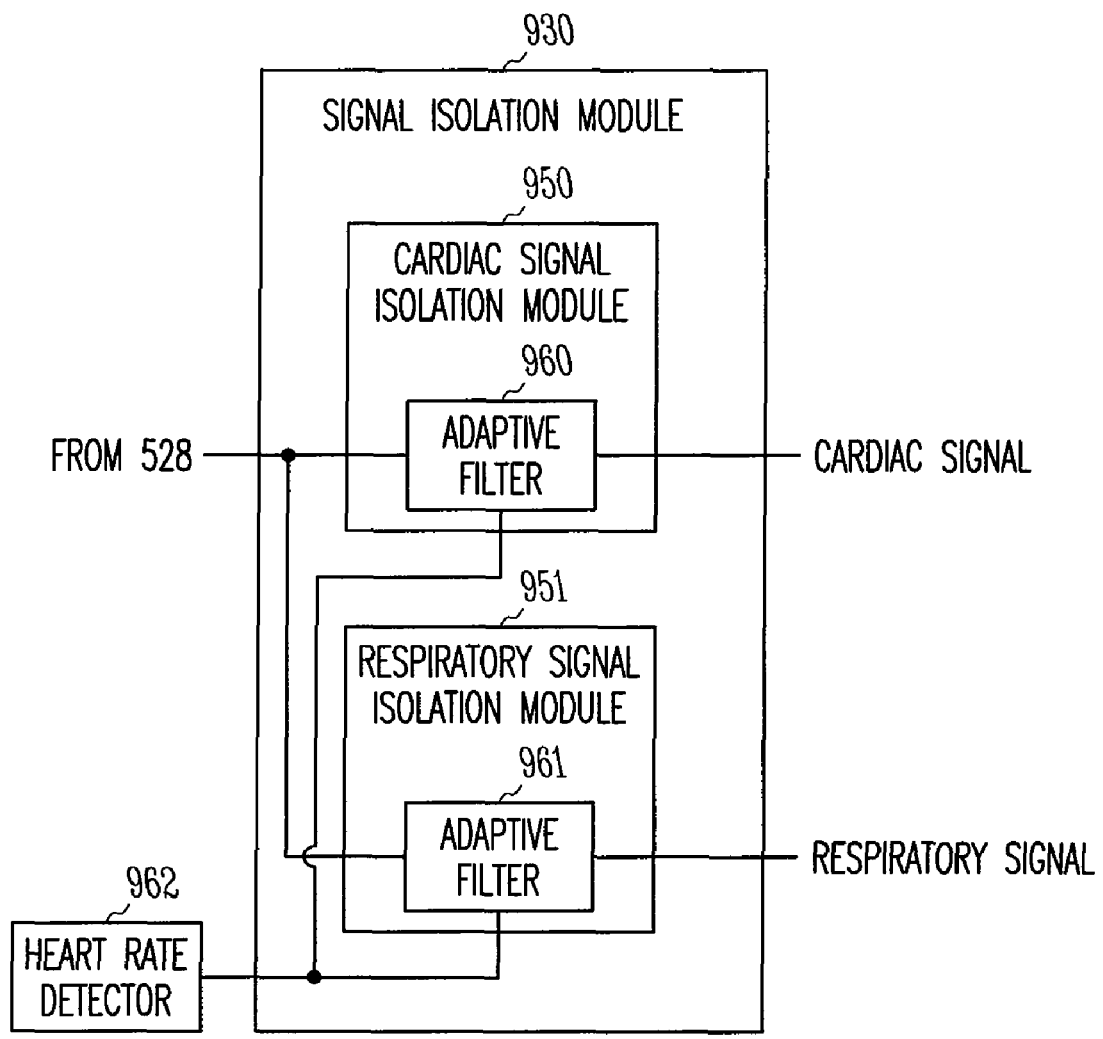
FIG. 9 is a block diagram illustrating another specific embodiment of portions of the system of FIG. 5 for isolating signals from the PAP signal.

FIG. 9 is a block diagram illustrating an embodiment of a signal isolation module 930 and a heart rate detector 962. Signal isolation module 930 is another specific embodiment of signal isolation module 530 and includes a cardiac signal isolation module 950 and a respiratory signal isolation module 951. While FIG. 3 shows that the spectrums of cardiac and respiratory signals overlap at around 1 Hz, the spectrums reflect the frequency characteristics over a range of heart rates, and it is observed that the spectrums of cardiac and respiratory signals do not substantially overlap at each specific heart rate. Thus, heart rate detector 962 detects a heart rate for use as a control signal for separating the cardiac and respiratory signals in the PAP signal using their frequency characteristics.

Cardiac signal isolation module 950 includes an adaptive filter 960. In one embodiment, adaptive filter 960 includes a band-pass filter having a dynamically adjustable pass band. In a specific embodiment, such an adaptive band-pass filter is used to isolate a cardiac signal indicative stroke volume. The pass-band includes a low cutoff frequency that is dynamically adjustable in a range of approximately 0.5 Hz to 1.0 Hz, and a high cutoff frequency that is approximately 20 Hz. In another embodiment, adaptive filter 960 includes a notch filter having a dynamically adjustable rejection band. In a specific embodiment, referring to FIG. 3, such an adaptive notch filter is used to isolate a cardiac signal indicative HF decompensation and stroke volume. The rejection band includes a low cutoff frequency that is approximately 0.0001 Hz and a high cutoff frequency that is dynamically adjustable in range of approximately 0.5 Hz to 1.0 Hz.

Respiratory signal isolation module 951 includes an adaptive filter 961. In one embodiment, adaptive filter 961 includes a band-pass filter having a dynamically adjustable pass band. In a specific embodiment, such an adaptive band-pass filter is used to isolate a respiratory signal indicative of tidal volume. The pass band includes a low cutoff frequency that is dynamically adjustable in a range of approximately 0.01 Hz, and the high cutoff frequency that is approximately 0.5 Hz to 1.0 Hz.

The pass bands of adaptive filters 960 and 961 are each dynamically adjustable using a physiological signal or parameter. In the embodiment illustrated in FIG. 9, heart rate detector 962 detects the heart rate as the physiological signal or parameter. That is, the pass bands of adaptive filters 960 and 961 are each a function of the heart rate and each adjusted in response to a substantial change in the detected heart rate.

Figure 10:
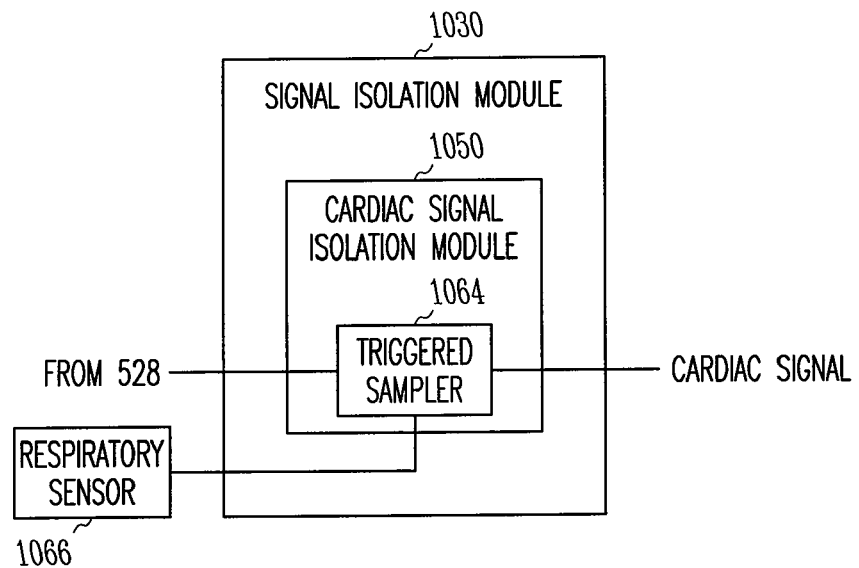
FIG. 10 is a block diagram illustrating another specific embodiment of portions of the system of FIG. 5 for isolating signals from the PAP signal.

FIG. 10 is a block diagram illustrating an embodiment of a signal isolation module 1030 and a respiratory sensor 1066. Signal isolation module 1030 is another specific embodiment of signal isolation module 530 and includes a cardiac signal isolation module 1050. Knowing the effects of respiration on the PAP signal, cardiac signal isolation module 1050 isolates a cardiac signal from the PAP by excluding the effects of the respiration. Respiratory sensor 1066 senses a respiratory signal indicative of respiratory cycles and pattern based on which the effects of respiration can be excluded. In general, effects of cyclic physiological signals such as those associated with cardiac and respiratory cycles can be substantially excluded or attenuated by triggered sampling.

Cardiac signal isolation module 1050 includes a triggered sampler 1064 that samples the PAP signal at a predetermined type event in each respiratory cycle. For example, the PAP signal is to be evaluated at the end of expiration to avoid the effects of respiration. By sampling the PAP signal at each end of expiration as indicated in the respiratory signal sensed by respiratory sensor 1066, triggered sampler 1064 isolates a cardiac signal from the PAP signal. In one embodiment, respiratory sensor 1066 is a minute ventilation sensor that is an implantable impedance sensor that senses an impedance indicative of lung volume.

Figure 11:
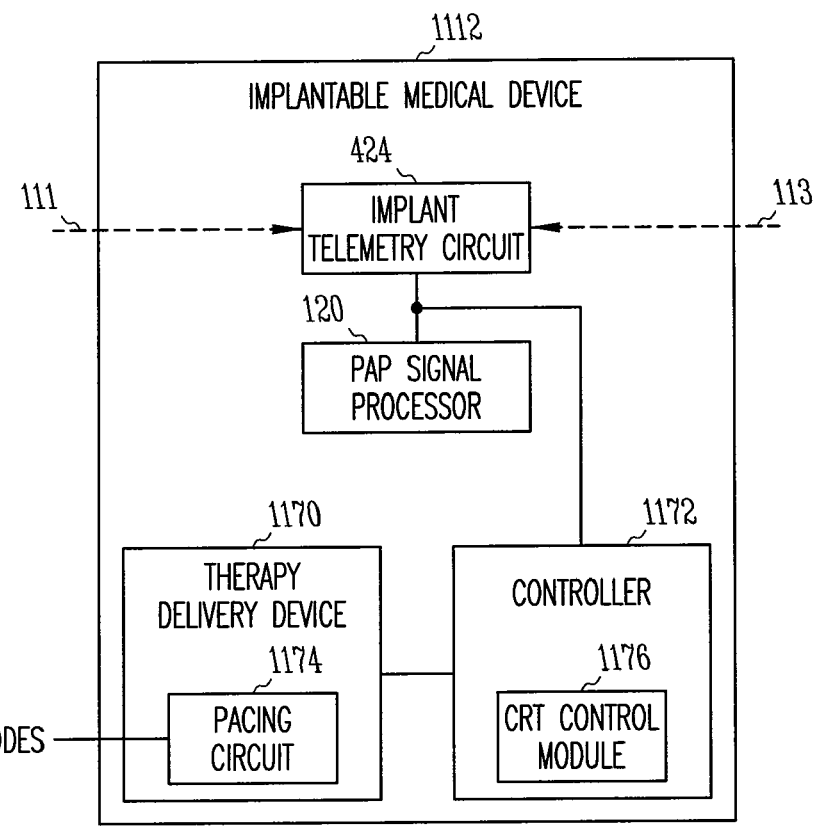
FIG. 11 is a block diagram illustrating an embodiment of portions of a circuit of an implantable medical device.

FIG. 11 is a block diagram illustrating an embodiment of portions of a circuit of an implantable medical device 1112, which is a specific embodiment of implantable medical device 112. Implantable medical device 1112 includes implant telemetry circuit 424, PAP signal processor 120, a therapy delivery device 1170, and a controller 1172.

Therapy delivery device 1170 delivers one or more therapies such as pacing therapy, cardioversion/defibrillation therapy, CRT, RCT, neural stimulation therapy, drug therapy, and biological therapy. Controller 1172 controls the delivery of the one or more therapies using at least one signal of the plurality of signals provided by PAP signal processor by isolation from the PAP signal received from implantable PAP sensor 110 via communication link 111. In one embodiment, therapy delivery device 1170 includes a pacing circuit 1174 to deliver pacing pulses, and controller 1172 includes a CRT control module 1176 to control the delivery of the pacing pulses by executing a CRT pacing algorithm.

Figure 12:
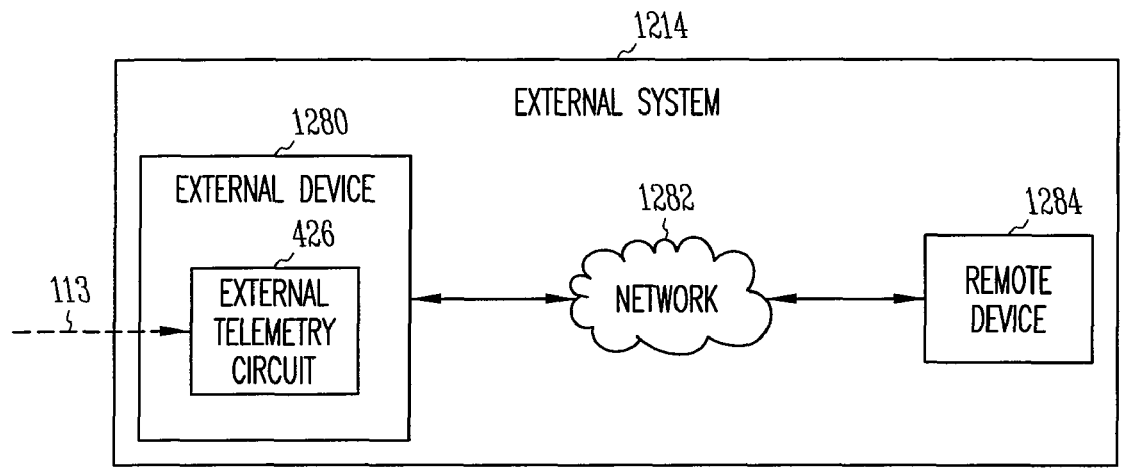
FIG. 12 is a block diagram illustrating an embodiment of an external system communicating with the implantable medical device.

FIG. 12 is a block diagram illustrating an embodiment of an external system 1214, which is a specific embodiment of external system 114. As illustrated in FIG. 12, external system 1214 is a patient management system including an external device 1280, a telecommunication network 1282, and a remote device 1284. External device 1280 is placed within the vicinity of the implantable medical device 112 and includes external telemetry system 426 to communicate with the implantable medical device 112 via telemetry link 113. Remote device 1284 is in one or more remote locations and communicates with external device 1280 through network 1282, thus allowing a user to monitor and treat a patient from a distant location and/or allowing access to various treatment resources from the one or more remote locations.

Figure 13:
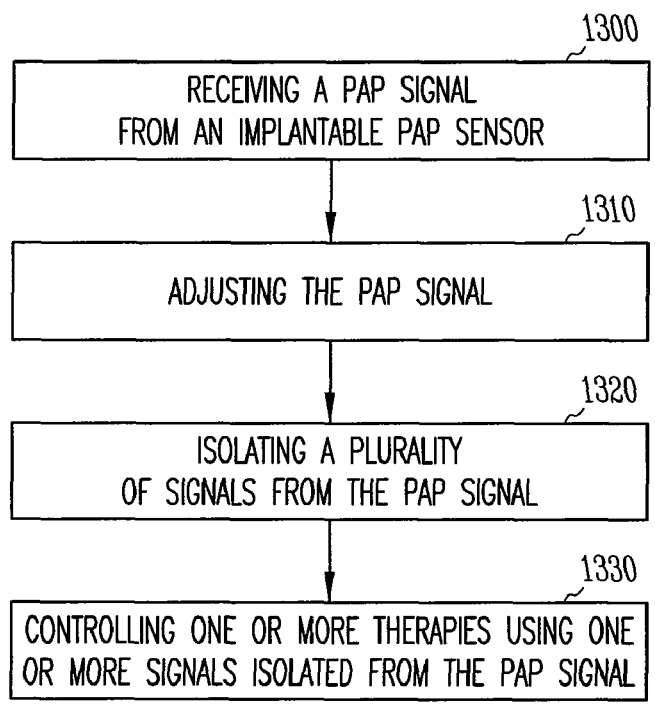
FIG. 13 is a flow chart illustrating an embodiment of a method for acquiring a plurality of signals using an implantable PAP sensor.

FIG. 13 is a flow chart illustrating an embodiment of a method for acquiring a plurality of signals using an implantable PAP sensor. In one embodiment, the method is performed by system 100.

A PAP signal is received from an implantable PAP sensor through a telemetry link at 1300. In one embodiment, the implantable PAP sensor is placed within the pulmonary artery to sense a PAP signal. In one embodiment, an ultrasonic signal is received through an ultrasonic telemetry link, and the PAP signal is received by demodulating the ultrasonic signal. In another embodiment, an electromagnetic signal is received through a far-field RF telemetry link, and the PAP signal is received by demodulating the electromagnetic signal. In another embodiment, a magnetic signal is received through an inductive telemetry link, and the PAP signal is received by demodulating the magnetic signal.

The PAP signal is adjusted at 1310. Examples of adjustment of the PAP signal include calibration for environmental factors, correction for effects of physiological activities or conditions, and pruning of known type outlier signal components. In one embodiment, the PAP signal is adjusted using an atmospheric pressure. In a further embodiment, the PAP signal is adjusted using a signal indicative of posture.

A plurality of signals is isolated from the PAP signal at 1320. The plurality of signals include, for example, one or more cardiac signals, one or more respiratory signals, an atmospheric pressure signal, a posture signal, a weather signal, an altitude signal, a Valsalva signal, and/or a Mueller signal. Such signals are each isolated from the PAP signal using its unique frequency, timing, and/or amplitude characteristics. In various embodiments, one or more signals are isolated from the PAP signal using a filter, based on their frequency characteristics illustrated in FIG. 3. In one embodiment, signals with frequency characteristics being functions of a detected physiological signal or parameter are isolated by filtering the PAP signal using one or more adaptive filters each having one or more characteristic frequencies that are dynamically adjustable using that physiological signal or parameter. In a specific embodiment, a cardiac signal and a respiratory signal are each isolated from the PAP signal by using such an adaptive filter with at least one cutoff frequency being dynamically adjustable in response to changes in a detected heart rate. In one embodiment, signals with timing characteristics related to a detected physiological signal or parameter are isolated by controlling the timing of the sampling of the PAP signal using that physiological signal or parameter. In a specific embodiment, one or more cardiac signals are isolated by sampling the PAP signal at a predetermined type event in each respiratory cycle detected from a sensed signal indicative of respiratory cycles.

One or more therapies are controlled using one or more signals isolated from the PAP signal at 1330. In one embodiment, the one or more therapies are delivered using an implantable medical device. In a specific embodiment, the implantable medical device performs steps 1300-1330. In another specific embodiment, the implantable medical device and an external system communicating with the implantable medical device perform steps 1300-1330. In another embodiment, an external system communicating with the implantable PAP sensor performs steps 1300-1330. Examples of the one or more therapies include pacing therapy, cardioversion/defibrillation therapy, CRT, RCT, neural stimulation therapy, drug therapy, and biological therapy. In one specific embodiment, pacing pulses are delivered according to a CRT algorithm using one or more signals isolated from the PAP signal.

FIGS. 14-29 illustrate exemplary embodiments of apparatus and method for delivering, positioning, and anchoring an implantable PAP sensor. These examples are also discussed in U.S. patent application Ser. No. 11/216,738, entitled "DEVICES AND METHODS FOR POSITIONING AND ANCHORING IMPLANTABLE SENSOR DEVICES," filed on Aug. 31, 2005, assigned to Cardiac Pacemakers, Inc., which is incorporated herein by reference in its entirety.

Figure 14:
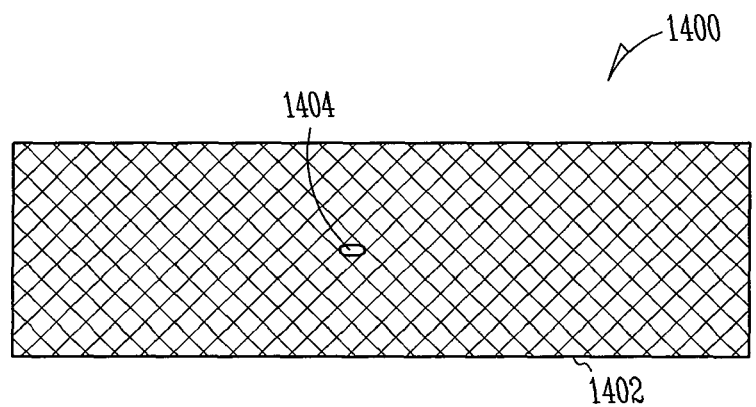
FIG. 14 illustrates a sensor anchoring device in accordance with one embodiment of the present invention.
Figure 15:
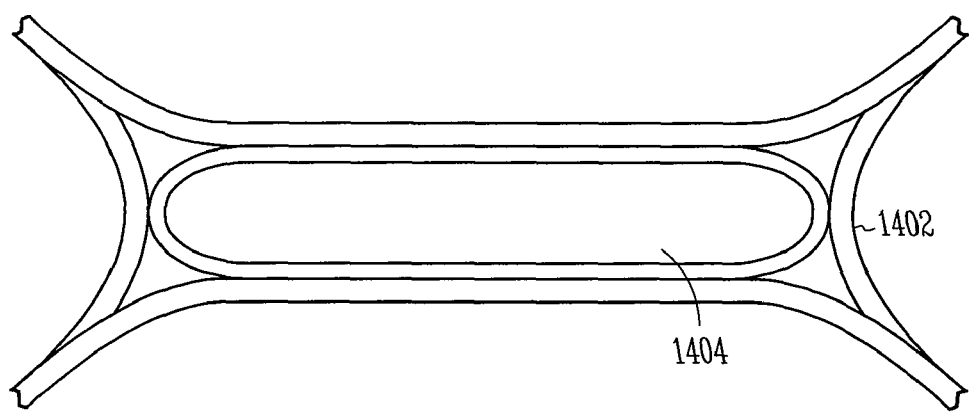
FIG. 15 is a top view of a section of the sensor anchoring device of FIG. 14 in which a sensor is placed.

FIG. 14 shows one embodiment of a physiologic sensor anchoring system 1400. In accordance with the illustrated embodiment, anchoring system 1400 comprises a stent-like structure 1402 carrying a physiologic parameter sensor 1404 (e.g., pressure sensor). The stent-like structure generally has a tubular shape like a stent, and is adapted to carry the sensor 1404 into a bodily vessel. In this particular embodiment, the physiologic parameter sensor 1404 is embedded in a mesh structure of the stent-like structure 1402, as is illustrated in a close-up view in FIG. 15.

Figure 16:
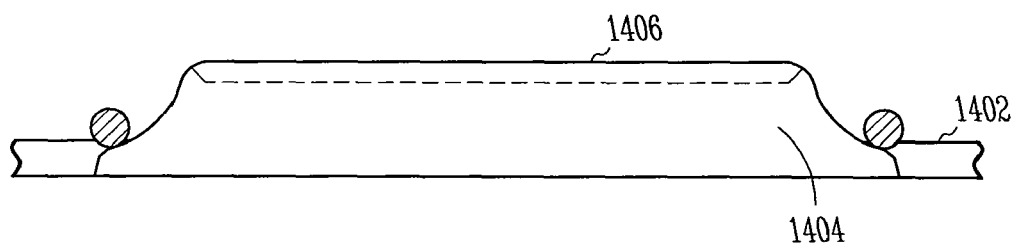
FIG. 16 is a side view of the sensor anchoring device section and sensor illustrated in FIG. 15.

The sensor 1404 may be secured to and carried by the stent-like structure 1402 in any number of ways. For example, as illustrated in FIG. 16, sensor 1404 can rest in a recessed diaphragm 1406 positioned in the stent 1402. In alternative embodiments, sensor 1404 can be secured within the stent using other securing mechanisms, such as adhesives, welding techniques, or the like. In addition, sensor 1404 is configured to communicate with implantable medical devices (IMDs), such as cardiac rhythm management device, and/or devices outside of a patient body. Examples of the sensors, sensor configurations, and communication systems and methods discussed in this document are discussed in more detail in U.S. patent application Ser. No. 10/943,626 entitled "SYSTEMS AND METHODS FOR DERIVING RELATIVE PHYSIOLOGIC PARAMETERS," U.S. patent application Ser. No. 10/943,269 entitled "SYSTEMS AND METHODS FOR DERIVING RELATIVE PHYSIOLOGIC PARAMETERS USING AN EXTERNAL COMPUTING DEVICE," U.S. patent application Ser. No. 10/943,627 entitled "SYSTEMS AND METHODS FOR DERIVING RELATIVE PHYSIOLOGIC PARAMETERS USING A BACKEND COMPUTING SYSTEM," and U.S. patent application Ser. No. 10/943,271 entitled "SYSTEMS AND METHODS FOR DERIVING RELATIVE PHYSIOLOGIC PARAMETERS USING AN IMPLANTED SENSOR DEVICE," and filed by Abhi Chavan et al., all assigned to Cardiac Pacemakers, Inc., which are incorporated herein by reference in their entirety and are collectively referred to as the "Physiologic Parameter Sensing Systems and Methods Patents" in this document.

In other embodiments, anchoring system 1400 may be used for the placement of IMDs with therapeutic functions such as actuating devices. For example, common actuators include, but are not limited to, an ultrasound sensor and a drug delivery pod. In some embodiments, anchoring system 1400 may be used to place a plurality of sensors, actuators, or a combination of sensors and actuators. Placement of multiple sensors and/or actuating devices throughout the body can allow for a more comprehensive therapeutic and diagnostic system, but multiple sensors and/or actuating devices are not required.

By using a stent-like anchoring structure, a sensor or any IMD can be anchored and secured in any part of the vascular system. In one particular embodiment, the stent-structure can be a balloon expandable stent, which can be placed in the vascular system using known catheterization techniques. For example, in one embodiment, the stent-structure can be positioned and secured in the pulmonary artery using techniques similar to a Swan Ganz technique, or other similar catheterization techniques. In this particular embodiment, when the stent-like anchoring mechanism 1402 is expanded, sensor 1404 will be place next to, or in close proximity to the vessel wall, allowing the sensor to obtain measurements from next to the vessel wall, which can be beneficial in many situations. As one skilled in the art will appreciate, for anchoring sensors in large cavities and/or arteries, stent-like anchoring mechanism 1402 may be larger than a traditional stent device. However, the device configuration can be similar.

A balloon deployable stent can be made of stainless steel, cobalt chromium, nitinol, and the like. The material composition of the stent may be determined based on a variety of factors. For example, a stent placed in an artery in a patient's neck typically has a shape-memory because the stent may be deformed by exogenous pressures. In contrast, a stent positioned in the heart will have the protection of the patient's rib cage to help protect the stent from outside forces. Thus, it is not as important for a stent that is positioned in the heart to be made of a memory retaining material.

The stent is typically located on the outside of the balloon. As such, while inflating the balloon the stent expands. In many instances, it is desirable to activate and test the sensor during the placement, or positioning, phase. However, one potential problem with the balloon expandable stent approach is that while the balloon is inflated, the blood flow through the artery may be reduced or completely blocked. Hence, the sensor may not be able to provide an accurate measurement during placement. In addition, if the procedure is complicated, positioning of the sensor or actuator may take more time than the patient can safely be with reduced blood flow, or without blood flow entirely, in that area.

The balloon composed of a semi-permeable or permeable membrane. For example, the balloon may have holes, or paths, which allow the blood to flow. Another possible solution is for the balloon to be in a shape, such as a cloverleaf shape, that provides pockets through which blood can continue to flow while the balloon is inflated. A cloverleaf shape will not completely block the artery, as blood will be able to flow between the pedals of the clover shaped balloon. These techniques allow the sensor to be activated and tested during the positioning of the device, some benefits of which are discussed below.

In some embodiments, by using a stent-like anchoring structure, a physician can perform two functions at once; i.e., use a stent to expand and support a vessel while placing a physiologic parameter sensor in a desired location. Also, using a stent-like structure can have additional benefits, such as, for example: (1) the stent structure, if coated with one or more drugs to minimize inflammation, can help inhibit the long term inflammation of artery or vessel tissue, which can occur when other anchoring techniques are used; (2) when using a self expanding stent, the sensor can be tested prior to anchoring, and if there are problems with the sensor, it can be retracted prior to deploying the stent-like anchoring device; (3) the controlled deployment of the stent-structure can prevent incorrect anchoring within the artery or vessel, which can lead to serious thrombolytic effects; and (4) the stent-like structure might assist in evoking a limited tissue growth response over the sensor anchor, thus holding the sensor in place (a further embodiment of this concept is discussed in more detail below).

In accordance with these embodiments of the invention, the specific type of stent and its anchoring location is not limited. For example, the stent-like structure can be made of titanium, stainless steel, nitinol, or some other suitable bio-compatible material, and the stent-like structure design is not limited to any particular configuration. Further, as discussed above, the stent-like structure can be place in any part of the vascular system, including but not limited to, any venous or aortic blood vessel, the pulmonary artery, blood vessels distal from the heart, or any cardiac separating or enclosing wall (e.g., the atrial septum). In addition, as discussed above, the sensor can be configured to measure any physiologic parameter value, including any physical, chemical or biologic property or parameter. Finally, in one embodiment, the stent-like structure and/or sensor can be coated with drugs or other materials, which can reduce thrombolytic or inflammatory effects, promote fibrosis, or the like.

Figure 17:
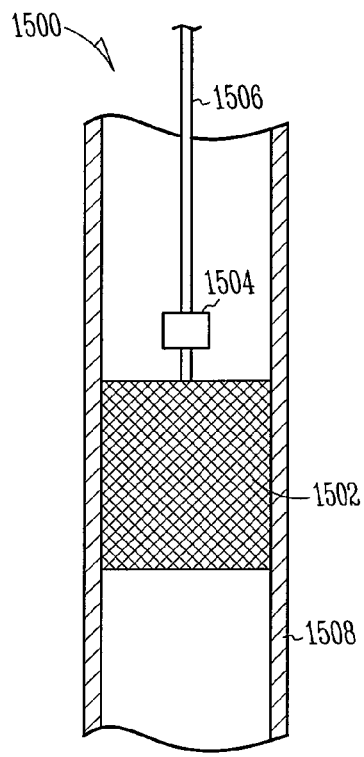
FIG. 17 is a cross-sectional view of one embodiment of a sensor anchoring device positioned within a bodily cavity.

FIG. 17 illustrates another embodiment of a physiologic parameter sensor and anchoring system 1500. In the embodiment illustrated in FIG. 17, system 1500 comprises an anchoring device 1502, a physiologic parameter sensor 1504, and one or more leads 1506 attached to sensor 1504. In this particular embodiment, anchoring device 1502 comprises a stent-like anchoring device, similar to the stent-like structure discussed above. In FIG. 17, anchoring device 1502 is shown expanded and anchored in a blood vessel 1508. Again, as discussed above, vessel 1508 can be any blood vessel within the body. In addition, anchoring device 1502 is not limited to stent-like structure. Other anchoring devices, such as the devices discussed below, also can be used. Further, embodiments of the present invention are not limited to obtaining physiologic measurements within blood vessels.

In this particular embodiment, sensor 1504 is attached or connected to lead 1506, and lead 1506 is further attached to anchoring device 1502. Thus, the purpose of anchoring device 1502 is to hold the sensor 1504 and lead 1506 configuration in a particular location in a vessel or other bodily cavity. As discussed in more detail in the Physiologic Parameter Sensing Systems and Methods Patents, lead 1506 can facilitate communication between sensor 1504 and an IMD, such as a cardiac rhythm management IMD. Lead 1506 can carry sensor measurements from sensor 1504 to the IMD, as well as therapy and/or other information from the IMD to the sensor 1504. Further, lead 1506 can be any suitable biocompatible lead (e.g., silicone, polyurethane, etc.) currently known or later developed.

Figure 18:
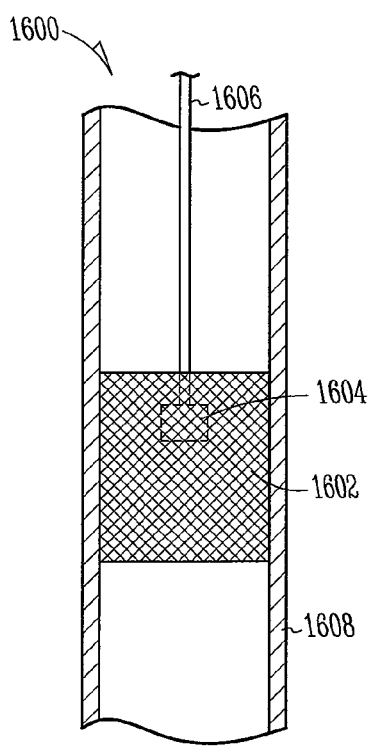
FIG. 18 is a cross-section view of another embodiment of a sensor anchoring device positioned within a bodily cavity.

FIG. 18 shows yet another embodiment of a physiologic parameter sensor and anchoring system 1600. In the embodiment illustrated in FIG. 18, system 1600 also comprises an anchoring device 1602, a physiologic parameter sensor 1604, and one or more leads 1606 attached to sensor 1604 and/or anchoring device 1602. According to various embodiments, the leads 1606 may be a conductor, such as a braided cable. Examples of material from which the tether may be formed include, but are not limited to, MP35N, stainless steel, and other standard lead conductors. According to some embodiments, the diameters of the leads 1606 typically range from 0.006 to 0.009 inches. In other embodiments, the diameters of the leads have a much larger range.

As with the embodiment illustrated in FIG. 17, anchoring device 1602 comprises a stent-like anchoring device, but other anchoring devices can be used. In FIG. 18, anchoring device 1602 is shown expanded and anchored in a blood vessel 1608. Again, as discussed above, vessel 1608 can be any blood vessel within the body, or any other bodily cavity, and embodiments of the present invention are not limited to obtaining physiologic measurements within blood vessels.

In this particular embodiment, sensor 1604 is connected to anchoring device 1602. Lead 1606 is attached to sensor 1604, and can be configured to communicate information to/from an IMD (e.g., a cardiac rhythm management IMD), as discussed in more detail in the Physiologic Parameter Sensing Systems and Methods Patents referenced above. For example, lead 1606 can carry sensor measurements from sensor 1604 to the IMD, as well as therapy and/or other information from the IMD to the sensor. Thus, one function of anchoring device 1602 is to hold the sensor 1604 in a particular location in a vessel or other bodily cavity, and one function of lead 1604 is to facilitate communication with the IMD.

Figure 19:
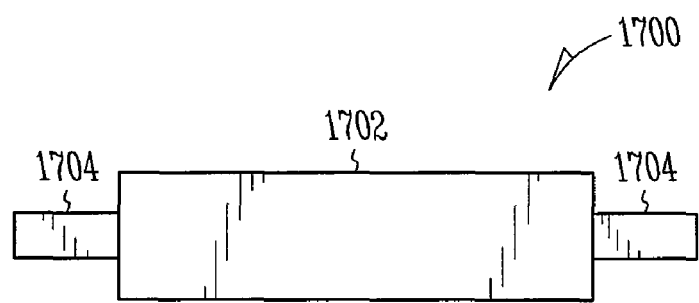
FIG. 19 is a view of one embodiment of a sensor device that can be anchored in a bodily cavity in accordance with one embodiment of the invention.

FIG. 19 illustrates one embodiment of a sensor device 1700 that can be positioned and anchored within a bodily cavity, such as a blood vessel, or the like. In the embodiment illustrated in FIG. 19, sensor device 1700 comprises a sensing mechanism (e.g., pressure sensor, circuitry, etc.) 1702 and one or more fins or extensions 1704 that can facilitate the anchoring of sensor device 1700 in a bodily vessel. In addition to fins 1704, the sensor 1700 may have a Dacron skirt (not shown) that promotes fibrous ingrowth/overgrowth. In one embodiment, the skirt is similar to those used on myocardial leads. By the time the stent bio-absorbs, such a skirt will have securely grown to the wall of the vessel. The Dacron skirt can be positioned on the bottom of the sensor 1700, but can also extend beyond the dimensions of the sensor 1700.

With regard to embodiments that include outwardly extending fins 1704, the stent-like structure 1706 may include sleeves (not shown) formed on a wall of the stent-like structure 1706 and configured for receiving and holding the fins 1704. Thus, the sensor device 1700 can be attached to the stent-like structure 1706 by sliding the fins 1704 into corresponding sleeves of the stent-like structure 1706. The sleeves may be configured to allow for tissue fibrosis, thereby enabling gradual tissue growth over the fins 1704 to secure the sensor device 1700 to a wall of the bodily vessel 1708.

Figure 20:
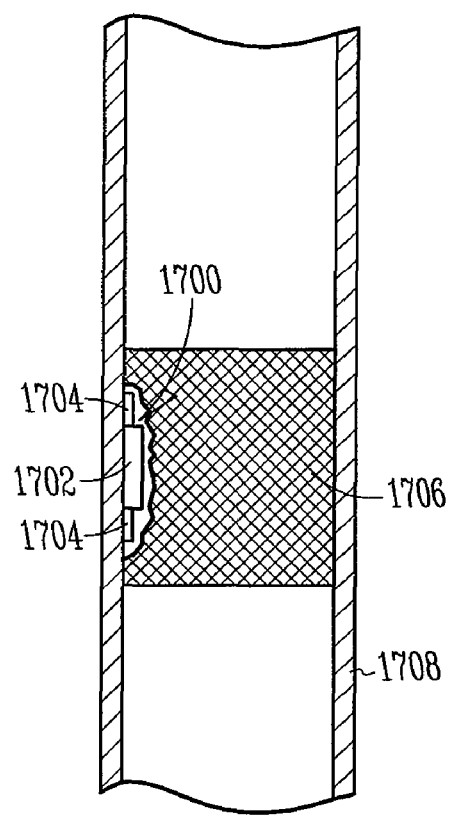
FIG. 20 is a cross-section view showing the sensor device of FIG. 19 being held in place in a bodily cavity by another embodiment of a sensor anchoring device.

According to some embodiments, the extension beyond the dimensions of the sensor 1700 is similar to the configuration in epicardial (EPI) leads. As shown in FIG. 20, sensor device 1700 can be positioned within the bodily vessel (e.g., blood vessel 1708 in FIG. 20), and initially anchored or held in place using an expandable stent-like structure 1706. As discussed above, stent-like structure 1706 can be any suitable stent device or other anchoring device currently known or later developed. In this particular embodiment, however, stent-like structure 1706 is bio-absorbable, and thus, will dissolve within a given time period (e.g., about 6-8 months).

In accordance with this particular embodiment, and as illustrated in FIG. 20, sensor device 1700 is connected to anchoring device 1706, so that sensor device 1700, and in particular, the one or more fins 1704, are positioned near the wall of vessel 1708. The device 1700 may be connected to the anchoring device 1706 by a tether, a mold, dissolvable sutures, and the like. In any event, by placing the fins or extensions 1704 near the vessel wall, tissue from the vessel will fibrose or grow over the fins 1704, securing the sensor device 1700 in the vessel. As one skilled in the art will appreciate, it may take time for fibrous tissue to form over extensions 1704. As such, a relatively slow dissolving bio-absorbable anchoring device 1706 is typically used to initially secure sensor device 1700 in place. As one skilled in the art will appreciate, the vessel tissue typically will fibrose over extensions 1704 within a period between about 3 months and 6 months, which is typically before anchor device 1706 will completely dissolve.

In one embodiment, sensor device 1700, including extensions 1704 are formed from a bio-compatible material, such as stainless steel, titanium, nitinol, or some other bio-compatible material. In some embodiments, sensor mechanism 1702 and extensions 1704 are formed of the same material. In other embodiments, sensor mechanism 1702 and extensions can be formed of different materials. In yet other embodiments, extensions 1704 can comprise dacron, nylon or other bio-compatible graphs or patches, making it easier for tissue to adhere thereto. As one skilled in the art will appreciate, any number of extension 1704 can be used, and extensions 1704 can be any suitable size, shape and/or material. Thus, embodiments of the present invention are not limited to any particular material or extension 1704 configuration illustrated and/or described herein. Further, in still other embodiments, sensor device 1700 can be coated with one or more drugs that might help reduce inflammation and/or encourage or facilitate tissue fibrosis. Such drugs are currently known in the art.

In some embodiments, a fabric, such as Gore-Tex® (gore), may be placed between the stent and the sensor or actuator. The placement of this fabric facilitates in keeping the tissue from attaching to the sensor itself and only allows the tissue to grow around the stent. As such, the sensor, actuator, or some part of the circuitry such as the battery, may be detached, removed or replaced during a surgical procedure at a later time. For example, in FIG. 14 the sensor or actuator 1402 may be removed, replaced, and reattached to anchoring mechanism 1402 with a new sensor or actuator. In some embodiments, gore may also be used to cover both sides of the stent. In these embodiments, the stent is sandwiched between two layers of gore and the physical expansion of the stent holds the device in place, even with the gore sheets on either side.

However, since tissue can not grow through the stent due to the gore, the entire stent may be more easily removed at a later time.

Figure 21:
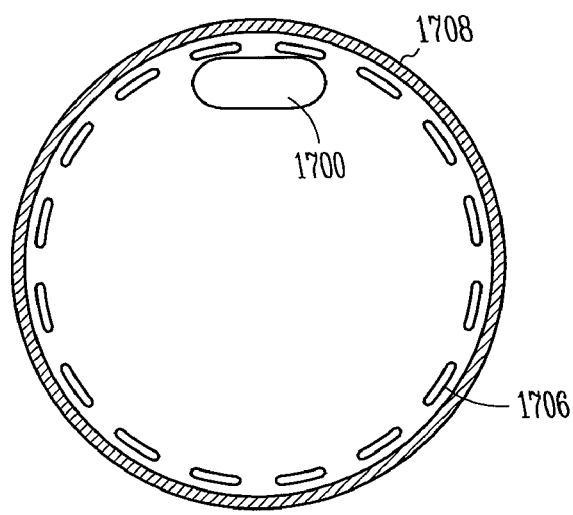
FIG. 21 is an axial view showing the sensor device of FIG. 19 being held in place in a bodily cavity in accordance with one embodiment of an anchoring device.

One embodiment, as illustrated in FIG. 20, has a sensor device 1700 placed within the anchoring structure 1706. FIG. 21 shows an axial view of this embodiment. However, the anchoring structure 1706 may be placed on one side of the sensor device 1700. Or, an anchoring structure may be attached to both sides of the sensor or actuator's extensions or fins 1704. This type of dual attachment of the sensor device 1700 to one or more anchoring structures 1706 may help facilitate more accurate final positioning of the sensor as both sides of the device may be anchored in place before the tissue grows around the device.

Figure 22:
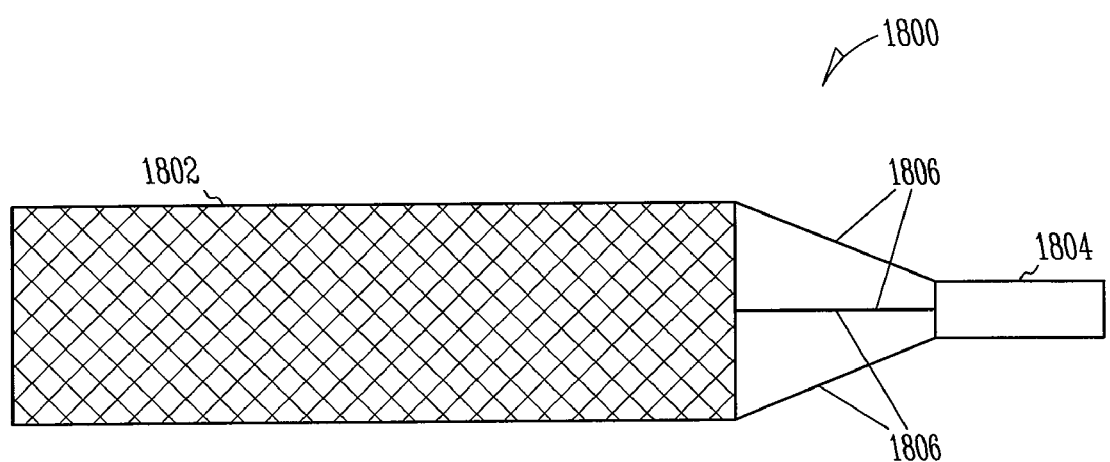
FIG. 22 is a view of another embodiment of a sensor anchoring device.

FIG. 22 shows yet another embodiment of an IMD anchoring system 1800. In this particular embodiment, anchoring system 1800 comprises an anchoring device 1802, a sensor 1804, and one or more connection structures 1806 for connecting sensor 1804 to anchoring device 1802. In this particular embodiment, connection structures 1806 are configured to secure sensor 1804 so that the sensor will reside near the middle of a blood vessel. By placing the sensor 1804 near the middle of the vessel, the sensor 1804 will reside in the predominant blood flow that occurs in the middle of the vessel, avoiding edge effects, such as slower blood flow, dead zones, and perhaps clotting issues.

In one embodiment, anchoring device 1802 can include a stent-like structure, as discussed above. Further, connection structures 1806 can comprise any structural configuration that will secure sensor 1804 in a desired location. For example, connection structures 1806 can comprise one or more strut-type structures configured to hold sensor 1804 in front of, or in back of anchoring device 1802. In this particular embodiment, the strut-type structures can be made of the same material as the stent-like structure 1802, or other materials can be used. Further, instead of securing sensor 1804 in front of, or in back of anchoring device 1802, connection structures can be used to secure sensor 1804 within anchoring device 1802, but still near the middle of the vessel. In addition, as discussed above, sensor 1804 can be configured to communicate with implantable medical devices (IMDs), such as cardiac rhythm management device, and/or devices outside of a patient body.

Figure 23:
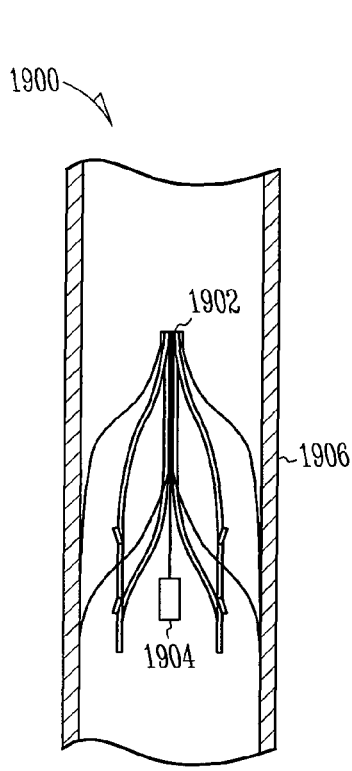
FIGS. 23-25 are cross-section views of yet other embodiments of sensor anchoring devices positioned within bodily cavities.
Figure 24:
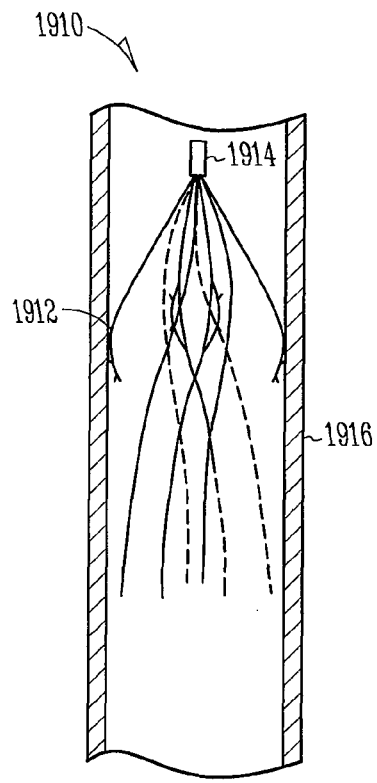
Figure 25:
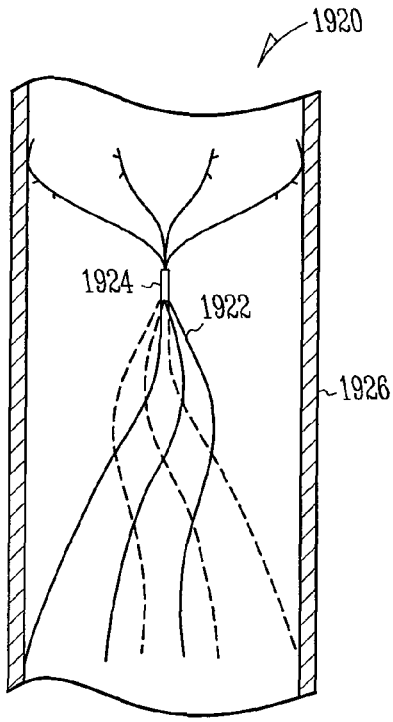

FIGS. 23-25 show additional embodiments of anchoring systems 1900, 1910, and 1920. In these embodiments, anchoring structures 1902, 1912, and 1922 can be used to secure sensors 1904, 1914, and 1924 within a bodily vessel (such as a blood vessel) 1906, 1916, and 1926, respectively. In some embodiments, the anchoring structure can be secured in place by surgical placement, and in other embodiments, the anchoring structure can be placed in a blood vessel, and then allowed to float or flow with the blood stream until the anchoring structure lodges in a suitable location to place the sensor.

In some embodiments (e.g., the embodiments illustrated in FIGS. 23-25), the anchoring structure can comprise a vena cava ("IVC") filter device having a sensor attached to it. For example, as illustrated in FIG. 23, a sensor 1904 can be connected to the IVC filter using a rigid or non-rigid tether connection. In other embodiments, such as the embodiments illustrated in FIGS. 24 and 25, sensors 1914 and 1924 can be incorporated into the structure of the IVC filter. In some embodiments, the sensor can be placed so that it is approximately near the center of the vessel to take advantage of the center flow of the vessel, and in other embodiments, the sensor can be configured so that it is secured near the wall of the vessel. Further, any suitable IVC filter device can be used. Examples of suitable IVC filters include, but are not limited to, an LGM filter, a Gunther tulipe filter, an Antheor filter, a DIL filter, a Keeper filter, a FCP2002 filter, a Mobin-Uddin filter, a Kimray-Greenfield filter, a Simon nitinol filter, a titanium Greenfield filter, a Bird's Nest filter, or any other suitable IVC filter device. Further, in other embodiments, the anchoring structures may not be IVC filters, but may comprise structures having legs or extensions for securing a sensor within a vessel. In these embodiments, the legs or extensions can be configured to lodge in the vessel in a manner similar to the IVC filters, thus securing the sensor in place.

In one embodiment, the anchoring structures are designed to be secured in the pulmonary artery, which branches and tapers as it flows toward the lungs. In this particular embodiment, the anchoring structure can be placed in the pulmonary artery, and then allowed to flow with blood stream until the anchoring structure lodges in a desired location. Once secured, the sensor can collect the desired data measurements. As one skilled in the art will appreciate, the size of the anchoring structure can control the location in which it will lodge. Also, as one skilled in the art will appreciate, the anchoring structure can be placed in other blood vessels, as well. Thus, embodiments of the present invention are not limited to use in the pulmonary artery.

A discussed above, sensors 1904, 1914 and 1924 can be configured to communicate with implantable medical devices (IMDs), such as cardiac rhythm management devices, and/or devices outside of a patient's body.

Figure 26:
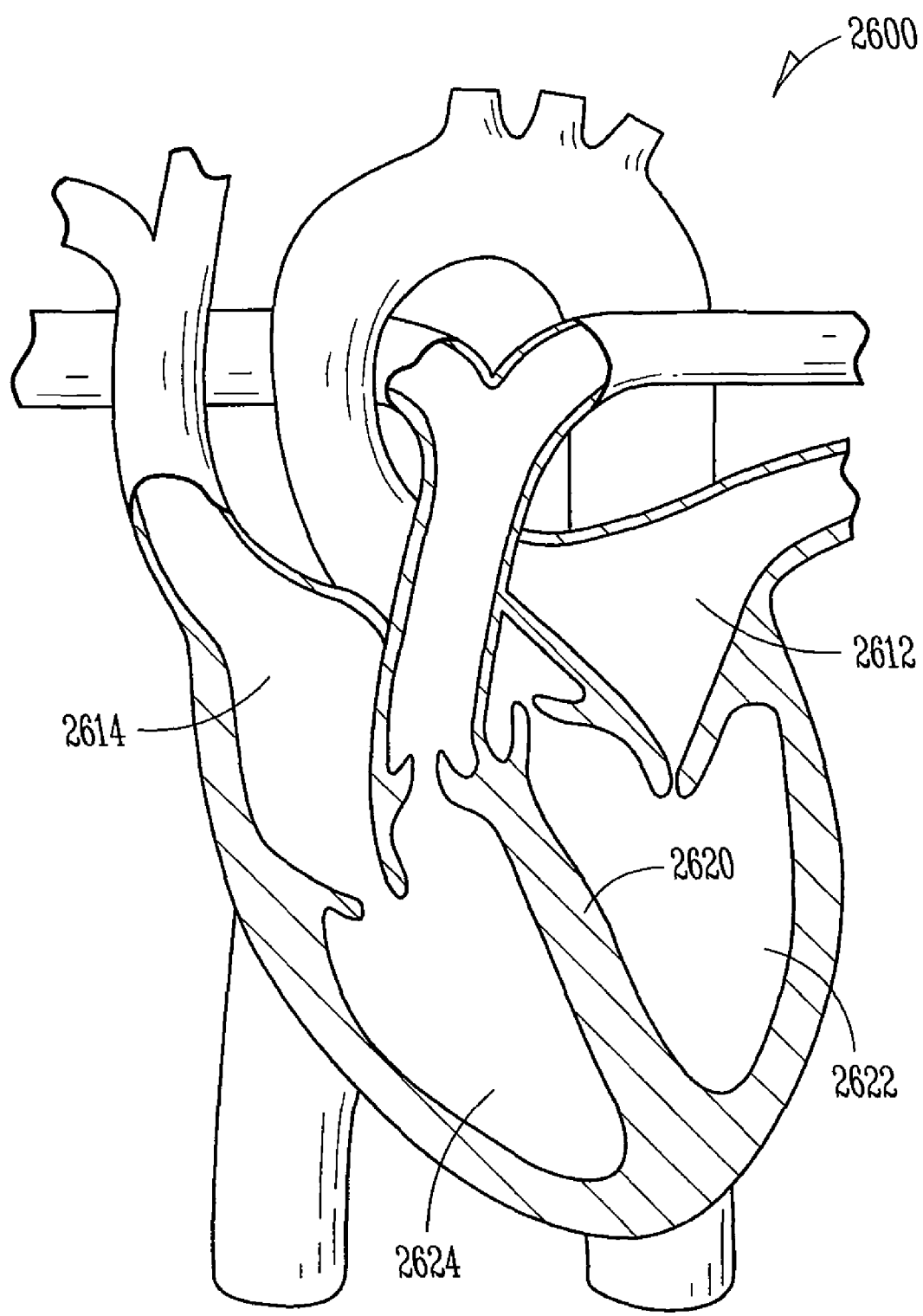
FIG. 26 is a cross-sectional view of a heart showing the septal walls.

FIG. 26 shows a cross-sectional view of a heart 2600. As illustrated, heart 2600 includes an atrium septal wall (not shown) separating left atrium 2612 from right atrium 2614, and a ventricular septal wall 2620 separating left ventricle 2622 from right ventricle 2624.

In accordance with another embodiment of the invention, a sensor anchoring device can be embedded in a separating or enclosing wall of the heart, for example, atrium septal wall or ventricular septal wall 2620. In FIGS. 27A-27E, one method of inserting a sensor anchoring device in accordance with this embodiment is shown. In this particular embodiment, a sensor 2708 can be embedded inside or attached to a plug-like anchoring structure, which then can be placed in any cardiac separating or enclosing wall 2704 (e.g., the septal wall). In accordance with this particular embodiment, a physician may be able to perform two functions at once: (1) fill a preexisting hole or slit in a cardiac separating wall in order to prevent blood from crossing from one side to another; and (2) use the plug as an enclosure for the placement of a physiologic parameter sensor. In other embodiments, a physician may create a hole or slit to place a sensor, and the plug-like anchoring structure can be used to place the sensor and plug and/or seal the slit or hole.

Figure 27A:
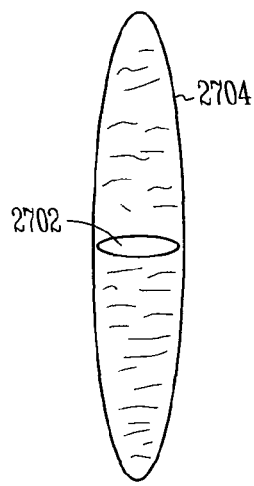
FIGS. 27A-27E are diagrams illustrating one embodiment of a method for anchoring a sensor within the septal wall of the heart.
Figure 27B:
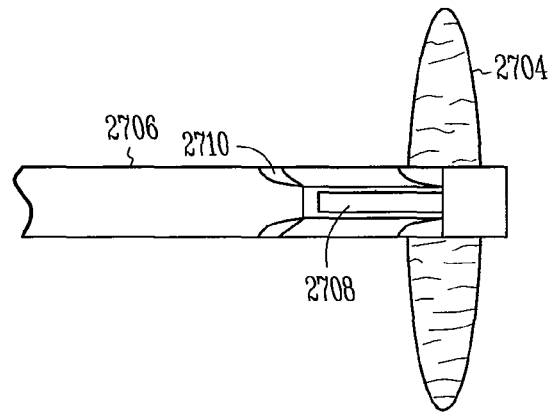
Figure 27C:
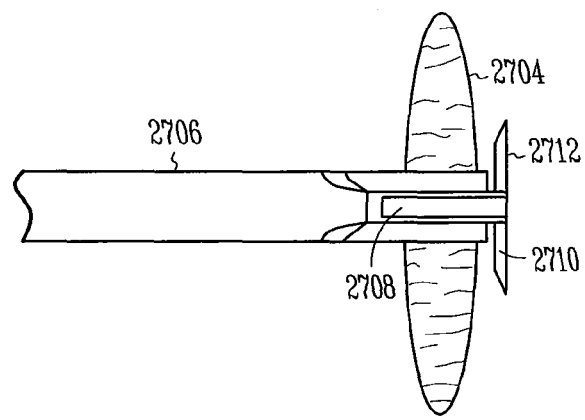
Figure 27D:
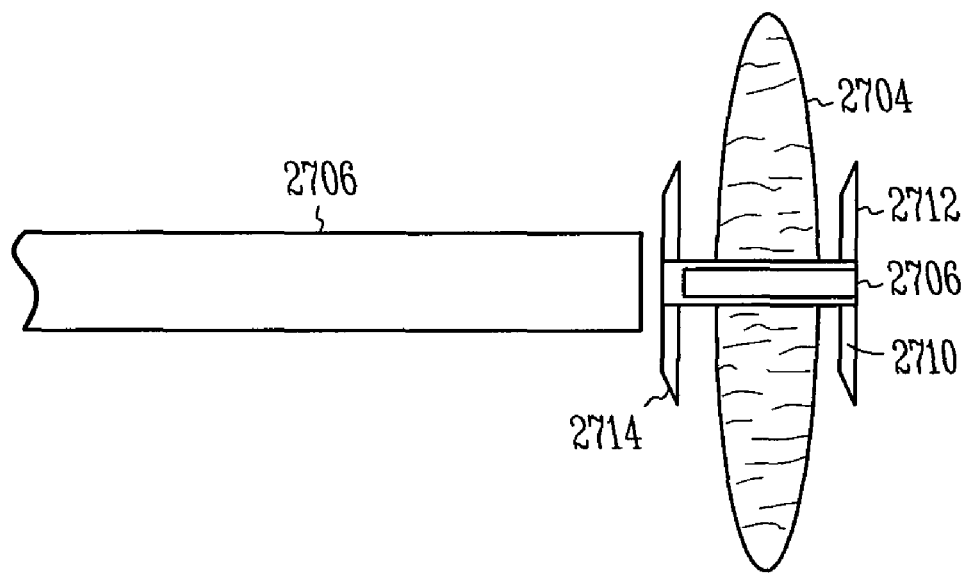

FIGS. 27A-27E illustrate one embodiment of a method for anchoring a sensor in a cardiac separating wall, such as the septal wall. FIG. 27A illustrates a cardiac separating wall (e.g., septal wall) 2704 with a hole or slit 2702 for placing an anchoring structure with sensor. As illustrated in FIG. 27B a physiologic parameter sensor 2708 embedded in or attached to a plug-like anchoring structure 2710 can be inserted into a pre-anchoring slit 2702 (either a nature hole or a surgically created hole or slit) using, for example, a guide catheter 2706. In this embodiment, the guide catheter has the anchor/sensor assembly embedded in it. To place the plug-like anchor 2710 (with sensor 2708) in the desired location, the guide catheter 2706 is placed in the hole or slit 2702 (FIG. 27B). Then, the guide catheter 2710 is retracted, causing plug ends 2712 and 2714 of the anchor device 2710 to expand (FIGS. 27C and 27D). The plug ends 2712 and 2714 form a seal so that blood cannot flow through hole 2702 or around anchor structure

Figure 27E:
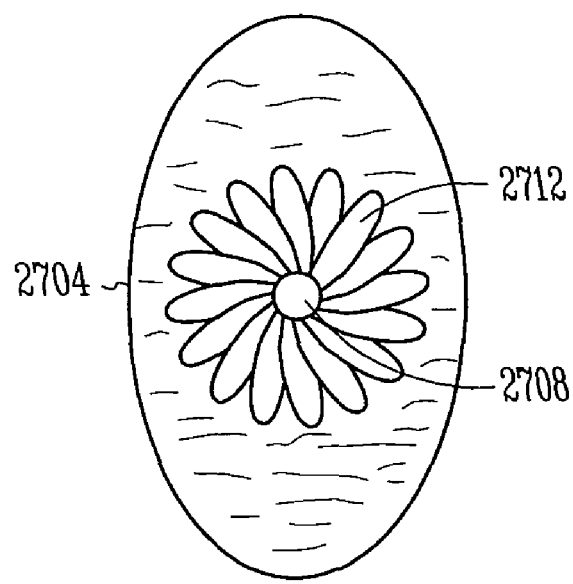

2710. FIG. 27E shows an end view of plug end 2712 of the anchoring device 2710. In one embodiment, the anchoring device can be a septal plug currently known in the art. In this embodiment, however, the septal plug is equipped with a sensor, as discussed.

Figure 28:
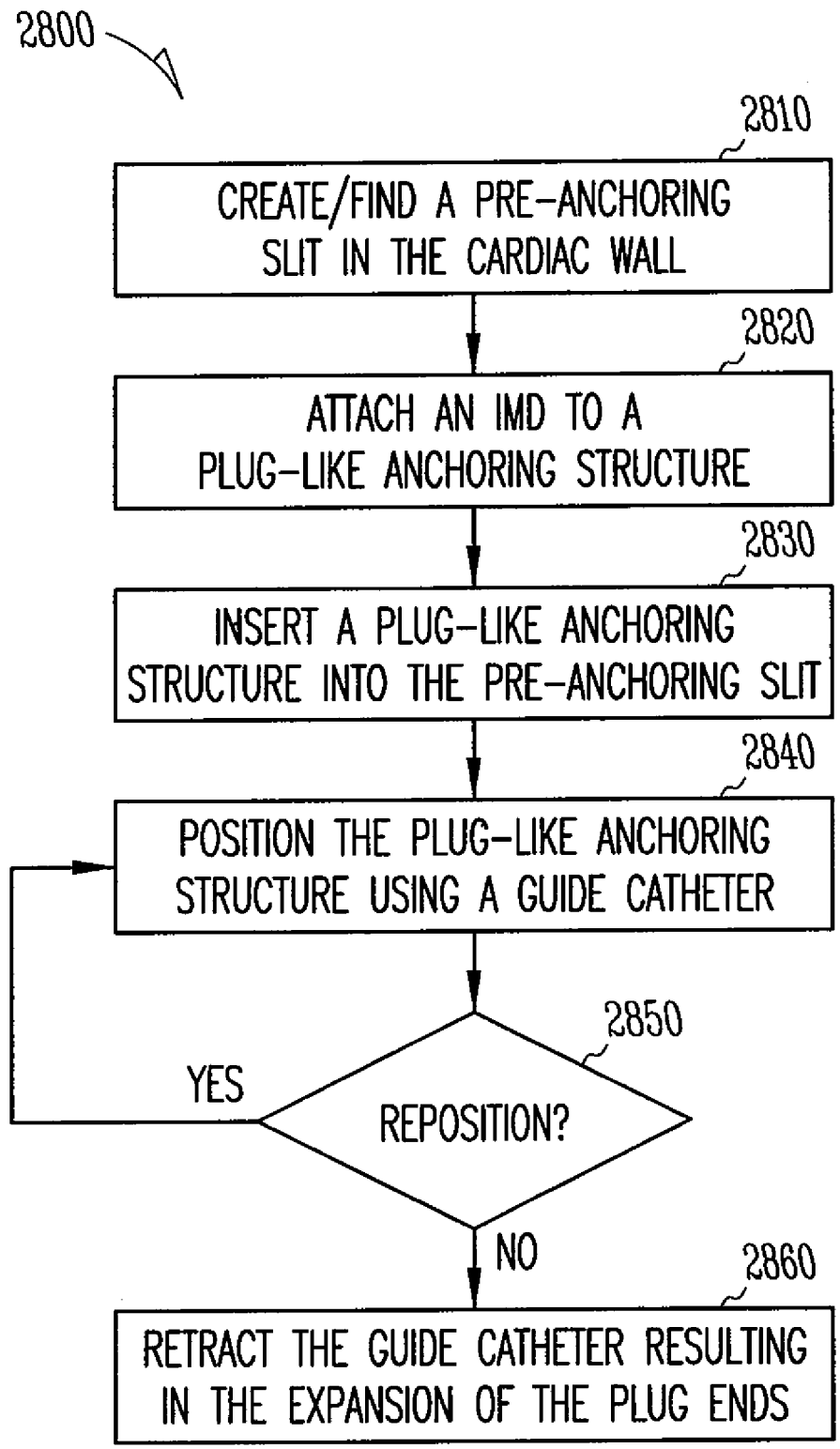
FIG. 28 is a flow diagram illustrating delivering, positioning, and anchoring a plug-like structure into a pre-anchoring slit according to one embodiment of the present invention.

FIG. 28 is a flow diagram 2800 illustrating delivering, positioning, and anchoring a plug-like structure into a pre-anchoring slit according to one embodiment of the present invention. At block 2810, a pre-anchoring slit is located, or surgically created if one does not exist, in the cardiac wall. An IMD is attached to a plug-like anchoring structure at step 2820. Then, the plug-like anchoring structure is inserted into the pre-anchoring slit at step 2830. At step 2840, using a guide catheter, the plug-like anchoring structure is positioned and then repositioned, at step 2850, as necessary. Once the final placement of the plug-like anchoring structure has been achieved, the guide catheter is retracted, resulting in the expansion of the plug ends at step 2860.

Figure 29:
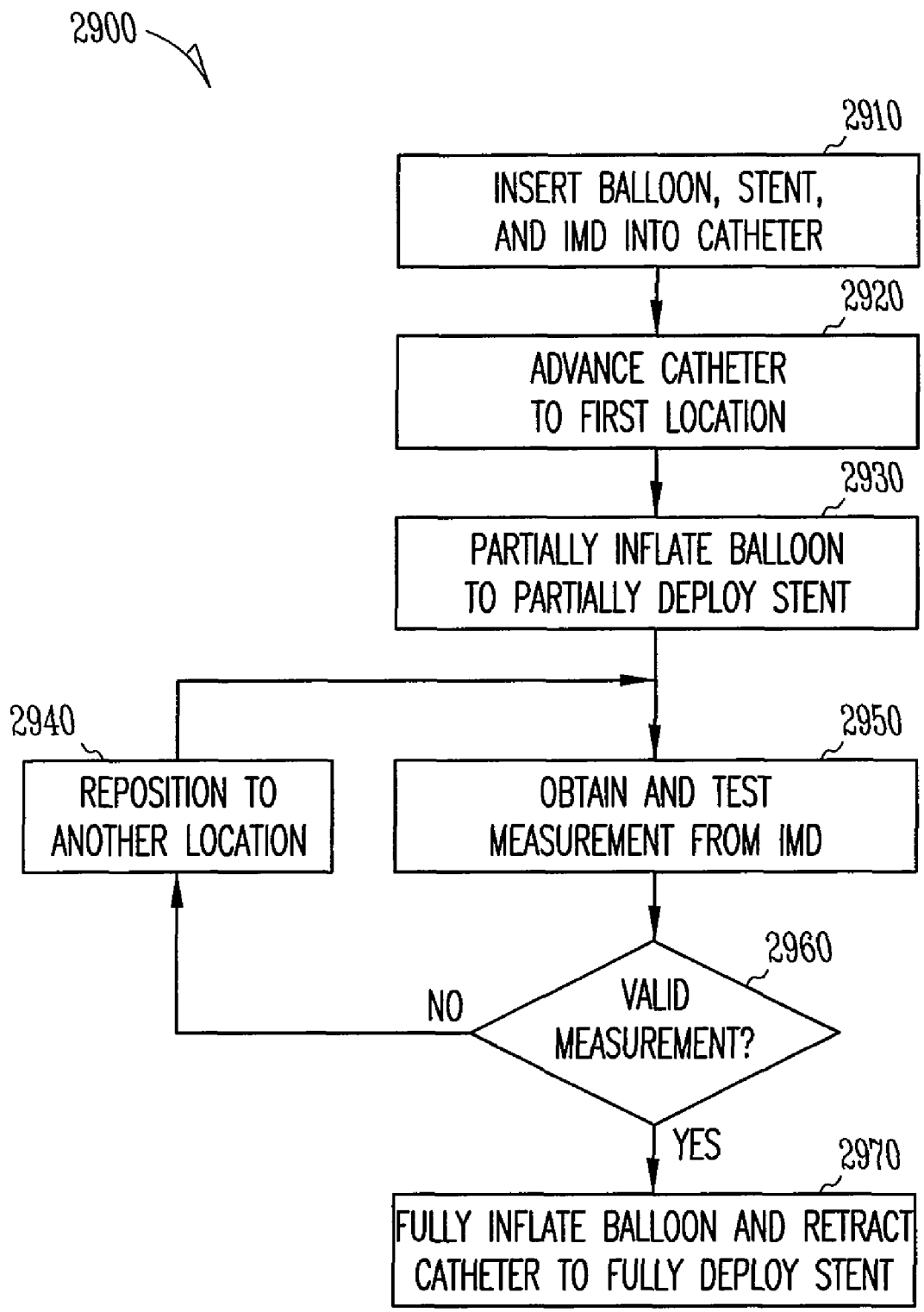
FIG. 29 is a flow diagram illustrating an exemplary algorithm for controllably positioning and anchoring an implantable medical device at a desired location.

FIG. 29 is a flow diagram illustrating an exemplary algorithm 2900 for controllably positioning and anchoring an IMD at a location in a bodily vessel. At block 2910, a deflated balloon is inserted through a collapsed stent and an IMD is attached to the stent using, for example, one of the attachment methods described above. The stent with balloon and IMD are then inserted into a catheter.

At block 2920, the catheter is advanced into the bodily vessel to a first location. The first location is typically selected to be close to the desired location. At block 2930, the balloon is partially inflated, thereby partially expanding the stent. By partially inflating the balloon, the positioning can be controlled by enabling later repositioning, if desired. With the balloon partially inflated, one or more physiologic parameter measurements are obtained from the IMD (e.g., blood pressure, temperature, strain, motion, etc.) at block 2950. The measurements are tested for validity. Testing the measurements can involve determining whether numerical values are detected and that the values are reasonable.

At decision block 2960, it is determined whether the measurements are valid. If the measurements are not valid, block 2940 repositions the stent to another location by moving the catheter. After the stent is repositioned to the other location, block 2950 again obtains and tests measurements from the IMD. Repositioning can continue until block 2960 determines that the measurements are valid. If the measurements are valid, the balloon is fully inflated at block 2970 at the current location. By fully inflating the balloon, the stent if fully expanded. The fully expanded stent frictionally engages with walls of the bodily vessel to secure the stent within the bodily vessel.

As discussed, FIG. 29 illustrates a process for positioning a sensor using a balloon-deployable stent. A different embodiment could include self-expanding stent that carries the sensor. In this embodiment, the self-expanding stent can be partially deployed and tested prior to full deployment. If test measurements taken after partial deployment are not informative, invalid, or for any other reason, considered undesirable, or for any other reason (e.g., patient discomfort), the self-expanding stent can be moved to another location, tested, and so on. When valid test measurements are obtained at a location, the stent can be fully expanded at that location.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "comprising" are open-ended, that is, a system, device, article, or process that includes elements in addition to those listed after such a term in a claim are still deemed to fall within the scope of that claim.

What is claimed is:

1. A method, comprising:
   receiving a pulmonary artery pressure (PAP) signal from an implantable PAP sensor through a wireless communication link;
   adjusting the PAP signal using a signal indicative of posture; and
   isolating a plurality of signals from the adjusted PAP signal using a signal processor.

2. The method of claim 1, wherein the plurality of signals comprises one or more cardiac signals and one or more respiratory signals.

3. The method of claim 2, wherein isolating the plurality of signals from the PAP signal comprises:
   isolating a cardiac signal using an adaptive filter having a pass-band; and
   adjusting the pass-band dynamically using a physiological signal or parameter.

4. The method of claim 2, wherein isolating the plurality of signals from the PAP signal comprises:
   isolating a respiratory signal using an adaptive filter having a pass-band; and
   adjusting the pass-band dynamically using a physiological signal or parameter.

5. The method of claim 1, comprising:
   receiving the PAP signal using an implantable medical device; and
   isolating the plurality of signals from the PAP signal using the implantable medical device.

6. The method of claim 1, wherein receiving the PAP signal comprises receiving an ultrasonic signal through an ultrasonic telemetry link and demodulating the ultrasonic signal.

7. The method of claim 1, wherein receiving the PAP signal comprises receiving an electromagnetic signal through a far-field radio-frequency telemetry link and demodulating the electromagnetic signal.

8. The method of claim 1, wherein receiving the PAP signal comprises receiving a magnetic signal through an inductive telemetry link and demodulating the magnetic signal.

9. The method of claim 1, further comprising adjusting the PAP signal using an atmospheric pressure before isolating the plurality of signals.

10. The method of claim 1, wherein isolating the plurality of signals comprises:
    filtering the PAP signal using at least one adaptive filter having a pass-band; and
    dynamically adjusting the pass-band using a physiological signal or parameter.

11. The method of claim 10, wherein dynamically adjusting the pass-band comprises:
    detecting a heart rate; and
    adjusting the pass-band dynamically as a function of the heart rate.

12. The method of claim 1, wherein isolating the plurality of signals comprises isolating the one or more cardiac signals by sampling the PAP signal at a predetermined type event in each cycle of a cyclic physiological signal.

13. The method of claim 1, wherein the plurality of signals comprises one or more of an atmospheric pressure signal, a posture signal, a weather signal, an altitude signal, a Valsalva signal, and a Mueller signal.

14. The method of claim 1, further comprising delivering one or more therapies using an implantable medical device.

15. The method of claim 14, further comprising controlling the delivery of the one or more therapies using one or more signals selected from the plurality of signals isolated from the PAP signal.

16. The method of claim 15, wherein the one or more therapies comprises a cardiac resynchronization therapy.

17. The method of claim 1, wherein isolating the plurality of signals comprises algorithmically pruning specified type outlier components from the PAP signal.

18. The method of claim 1, wherein receiving the PAP signal from the implantable PAP sensor comprises receiving the PAP signal from a sensor positioned within a pulmonary artery.

19. The method of claim 18, wherein receiving the PAP signal from the implantable PAP sensor comprises receiving the PAP signal from a sensor secured to an anchoring system having a stent-like structure configured to be secured in the pulmonary artery.

* * * * *